US010509029B2

(12) United States Patent
Tamura

(10) Patent No.: US 10,509,029 B2
(45) Date of Patent: Dec. 17, 2019

(54) MEASUREMENT DEVICE AND MEASUREMENT METHOD

(71) Applicant: TOKYO ELECTRON LIMITED, Tokyo (JP)

(72) Inventor: Akitake Tamura, Tokyo (JP)

(73) Assignee: TOKYO ELECTRON LIMITED, Tokyo (JP)

( * ) Notice: Subject to any disclaimer, the term of this patent is extended or adjusted under 35 U.S.C. 154(b) by 0 days.

(21) Appl. No.: 15/314,008

(22) PCT Filed: May 1, 2015

(86) PCT No.: PCT/JP2015/063082
§ 371 (c)(1),
(2) Date: Nov. 25, 2016

(87) PCT Pub. No.: WO2015/182334
PCT Pub. Date: Dec. 3, 2015

(65) Prior Publication Data

US 2017/0191993 A1 Jul. 6, 2017

(30) Foreign Application Priority Data

May 28, 2014 (JP) ................................ 2014-110583

(51) Int. Cl.

*G01N 33/543* (2006.01)
*G01N 21/64* (2006.01)

(Continued)

(52) U.S. Cl.
CPC ..... *G01N 33/54313* (2013.01); *G01N 1/2211* (2013.01); *G01N 1/28* (2013.01);
(Continued)

(58) Field of Classification Search
CPC ............. G01N 33/15; G01N 33/56983; G01N 33/582; G01N 21/6486; G01N 21/6428;
(Continued)

(56) References Cited

U.S. PATENT DOCUMENTS 4,941,899 A * 7/1990 Liu ...................... G01N 1/2211 55/337
5,063,164 A * 11/1991 Goldstein .............. G01N 31/22 422/401

(Continued)

FOREIGN PATENT DOCUMENTS

| | | | |
|---|---|---|---|
| EP | 2634580 | A1 | 9/2013 |
| EP | 2679985 | A2 | 1/2014 |
| WO | 2012056641 | A1 | 5/2012 |

OTHER PUBLICATIONS

International Search Report dated Aug. 4, 2015 corresponding to International Application No. PCT/JP2015/063082.

*Primary Examiner* — Mohamed K Amara
(74) *Attorney, Agent, or Firm* — Nath, Goldberg & Meyer; Jerald L. Meyer

(57) ABSTRACT

Provided is a measurement device, including: a droplet forming part configured to form aerosol-like liquid droplets from a liquid in which a fluorescent substance specifically bondable to detection target particles and a specimen are mixed with each other; a droplet sorting part configured to sort droplets having a diameter smaller than a predetermined value from the droplets formed by the droplet forming part; and a measurement part configured to irradiate light onto the droplets sorted by the droplet sorting part and configured to measure the fluorescence intensity of the droplets.

12 Claims, 18 Drawing Sheets

Figure 2A:
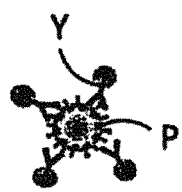
Figure 2B:
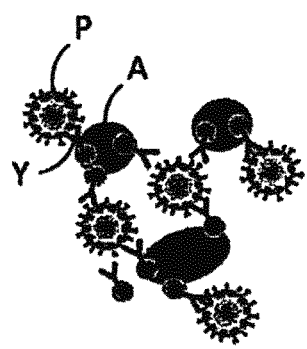

(51) Int. Cl.
*G01N 33/58* (2006.01)
*G01N 1/22* (2006.01)
*G01N 1/28* (2006.01)
*G01N 15/14* (2006.01)
*G01N 15/00* (2006.01)

(52) U.S. Cl.
CPC ......... *G01N 15/1459* (2013.01); *G01N 21/64* (2013.01); *G01N 21/6428* (2013.01); *G01N 21/6486* (2013.01); *G01N 33/54366* (2013.01); *G01N 33/54393* (2013.01); *G01N 33/582* (2013.01); *G01N 2001/2223* (2013.01); *G01N 2015/0026* (2013.01); *G01N 2015/0046* (2013.01); *G01N 2015/1481* (2013.01); *G01N 2021/6439* (2013.01)

(58) Field of Classification Search
CPC ..... G01N 33/54386; G01N 2021/6439; G01N 33/54313; G01N 33/54366; G01N 33/54393
See application file for complete search history.

(56) References Cited

U.S. PATENT DOCUMENTS

| | | | | |
|---|---|---|---|---|
| 5,563,350 A * | 10/1996 | Kashimura | ........... | G01F 1/3209 285/49 |
| 6,060,598 A * | 5/2000 | Devlin | ............... | A61K 49/0015 436/172 |
| 6,103,534 A * | 8/2000 | Stenger | ................. | G01N 21/76 422/52 |
| 6,217,636 B1 * | 4/2001 | McFarland | .......... | G01N 1/2211 55/339 |
| 6,514,721 B2 * | 2/2003 | Spurrell | ................ | G01N 1/2205 435/287.5 |
| 6,517,593 B1 * | 2/2003 | Robertson | ................ | C12Q 1/04 435/30 |
| 6,532,835 B1 * | 3/2003 | Saaski | ................. | G01N 1/2273 73/863.21 |
| 7,250,138 B2 * | 7/2007 | Wick | ................. | G01N 1/2273 422/50 |
| 7,410,805 B2 * | 8/2008 | Tanielian | ............ | G01N 1/2202 436/165 |
| 7,428,971 B2 * | 9/2008 | Hirano | ............... | G01N 15/1456 209/142 |
| 7,846,228 B1 * | 12/2010 | Saaski | .................... | B01D 46/10 55/400 |
| 7,964,018 B2 * | 6/2011 | Kang | .................... | B01D 45/12 95/13 |
| 8,176,766 B1 * | 5/2012 | Ruiz | .................... | G01N 33/497 422/84 |
| 8,459,098 B2 * | 6/2013 | Lee | .................... | G01N 1/2211 73/23.3 |
| 8,535,938 B2 * | 9/2013 | Durack | ................ | C12N 5/0612 422/67 |
| 8,539,840 B2 * | 9/2013 | Ariessohn | ................ | B08B 3/12 73/860 |
| 8,691,584 B2 * | 4/2014 | Durack | .................. | G01N 33/48 422/73 |
| 8,772,738 B2 * | 7/2014 | Ozasa | .................. | G01N 15/147 250/458.1 |
| 9,028,758 B2 * | 5/2015 | Keinan | ................ | G01N 1/2211 422/86 |
| 9,250,174 B2 * | 2/2016 | Sekimoto | ............... | G01N 15/10 |
| 9,328,322 B2 * | 5/2016 | Verdier | ............... | G01N 1/2208 |
| 9,671,320 B2 * | 6/2017 | Yang | .................... | G01N 1/2202 |
| 9,909,956 B1 * | 3/2018 | St Amant, III | ....... | G01N 1/2211 |
| 2002/0018211 A1 * | 2/2002 | Megerle | ................ | G01N 15/14 356/440 |
| 2002/0078826 A1 * | 6/2002 | Day | ...................... | B01D 45/12 95/219 |
| 2004/0069047 A1 * | 4/2004 | Coyle | ................. | B01D 50/004 73/28.04 |
| 2006/0057599 A1 * | 3/2006 | Dzenitis | ............... | G01N 1/2202 435/6.18 |
| 2006/0123752 A1 * | 6/2006 | Symonds | ............... | B01D 45/16 55/434.2 |
| 2006/0144025 A1 * | 7/2006 | Vallayer | ................. | B01D 45/12 55/428 |
| 2006/0154234 A1 * | 7/2006 | Winther | ................... | G01N 1/36 435/4 |
| 2006/0257287 A1 * | 11/2006 | Call | ...................... | B01D 45/04 422/83 |
| 2007/0068223 A1 * | 3/2007 | Chen | ................... | G01N 1/2211 73/30.01 |
| 2007/0122349 A1 * | 5/2007 | Wachtel | ............. | G01N 15/0205 424/45 |
| 2009/0317735 A1 * | 12/2009 | Ohtani | ................. | G03G 9/0804 430/105 |
| 2010/0015601 A1 * | 1/2010 | Gilmore | ................ | G01N 1/2202 435/6.16 |
| 2011/0039679 A1 * | 2/2011 | Pierson | ................ | G01N 1/2211 494/10 |
| 2011/0092376 A1 * | 4/2011 | Colston, Jr. | ........... | B01F 3/0807 506/7 |
| 2012/0088691 A1 * | 4/2012 | Chen | ....................... | B01L 7/52 506/12 |
| 2014/0151543 A1 * | 6/2014 | Nagano | ................ | G01N 1/2214 250/282 |
| 2014/0163664 A1 * | 6/2014 | Goldsmith | ....... | A61B 17/00491 623/1.11 |
| 2016/0274006 A1 * | 9/2016 | Sompuram | ...... | G01N 33/54313 |
| 2017/0191993 A1 * | 7/2017 | Tamura | ........... | G01N 33/54313 |

* cited by examiner

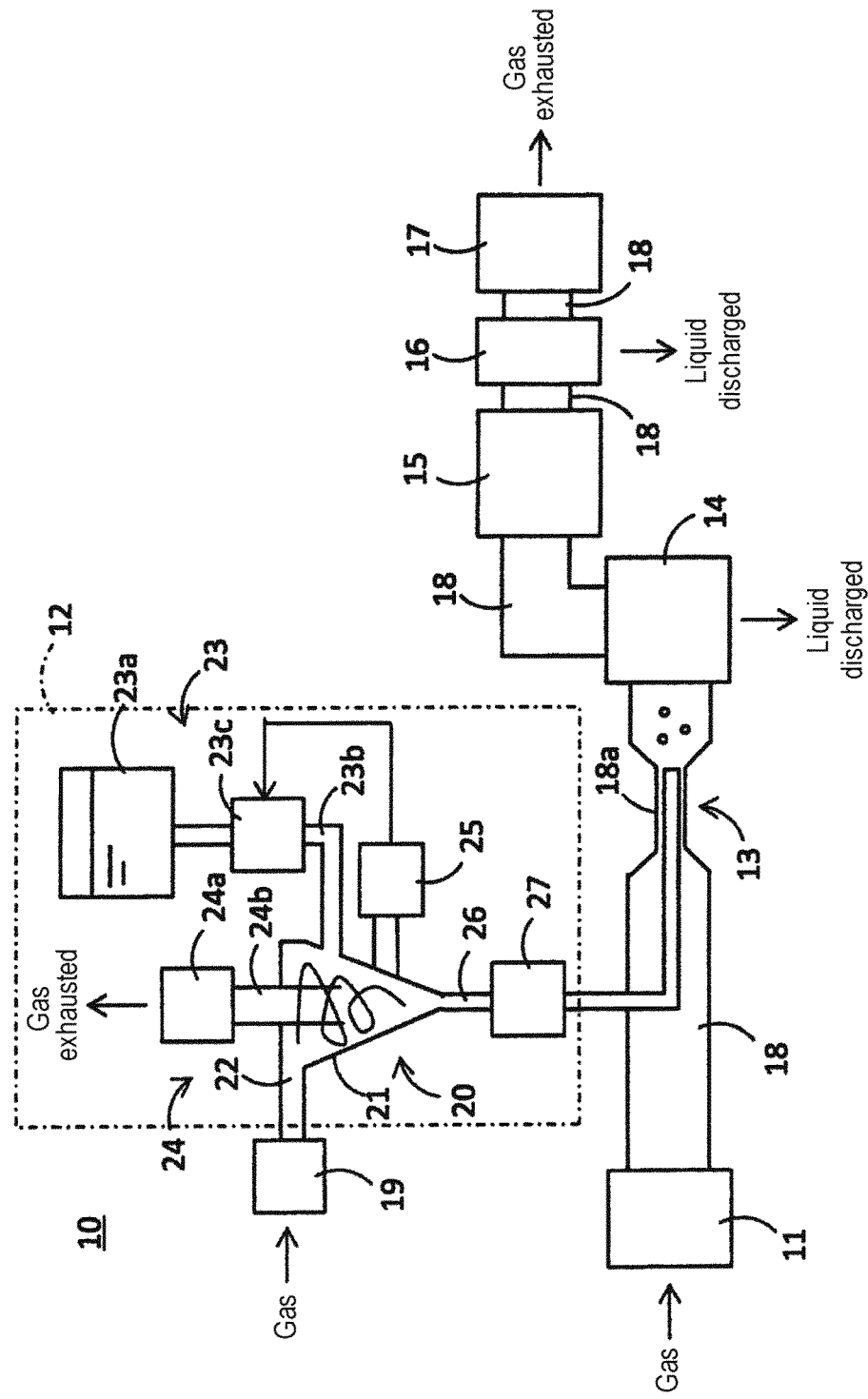

MEASUREMENT DEVICE AND MEASUREMENT METHOD

TECHNICAL FIELD

The present disclosure relates to a measurement device and a measurement method.

BACKGROUND

In the related art, a detection method for detecting detection target particles to be detected is known. As a detection method, a method which makes use of fluorescence-labeled antibodies specifically bonded to detection target particles to be detected is known. In the method using the fluorescence-labeled antibodies, for example, a drug solution containing fluorescence-labeled antibodies specifically bonded to viruses is brought into contact with an inspection target gas so that the viruses existing in the gas are diffused into the drug solution. Thus, a mist group of the drug solution, in which the viruses are diffused, is formed and the fluorescence intensity thereof is measured. The viruses are detected depending on the fluorescence intensity (see, e.g., International Publication No. 2012/056641).

SUMMARY

In this regard, there is a need to improve the detection accuracy of detection target particles.

According to one embodiment of the present disclosure, there is provided a measurement device, including: a droplet forming part configured to form aerosol-like liquid droplets from a liquid in which a fluorescent substance specifically bondable to detection target particles and a specimen are mixed with each other; a droplet sorting part configured to sort droplets having a diameter smaller than a predetermined value from the droplets formed by the droplet forming part; and a measurement part configured to irradiate light onto the droplets sorted by the droplet sorting part and configured to measure a fluorescence intensity of the droplets.

According to another embodiment of the present disclosure, there is provided a measurement method, including: a droplet forming step of forming aerosol-like liquid droplets from a liquid in which a fluorescent antibody specifically bondable to detection target particles and a specimen are mixed with each other; a droplet sorting step of sorting droplets having a diameter smaller than a predetermined value from the droplets formed at the droplet forming step; and a measurement step of irradiating light onto the droplets passed through the droplet sorting step and measuring a fluorescence intensity of the droplets.

BRIEF DESCRIPTION OF THE DRAWINGS

FIG. 1 is a schematic view illustrating a configuration of a measurement device according to a first embodiment of the present disclosure.

FIG. 2A is a schematic diagram illustrating a state in which a fluorescent substance is bonded to a detection target particle.

FIG. 2B is a schematic diagram illustrating a state in which antibody agglomeration particles are bonded to detection target particles.

FIG. 3 is a schematic view illustrating a modification of a configuration of a droplet forming part of the measurement device illustrated in FIG. 1.

FIG. 4 is a perspective view illustrating a configuration of a droplet sorting part of the measurement device illustrated in FIG. 1.

FIG. 5 is an internal configuration diagram illustrating a configuration of a measurement part of the measurement device illustrated in FIG. 1.

FIG. 6 is a schematic diagram for explaining the fluorescence intensity in the case where the diameter of droplets is relatively large.

FIG. 7 is a schematic diagram for explaining the fluorescence intensity in the case where the diameter of droplets is relatively small.

FIG. 8 is a graph illustrating the measurement results of the fluorescence intensity in an example using the measurement device illustrated in FIG. 1.

FIG. 9 is a graph overlappingly illustrating the measurement results of the fluorescence intensity in an example in which the measurement device illustrated in FIG. 1 is used and a comparative example in which a particle sorting part is omitted from the measurement device illustrated in FIG. 1.

FIG. 10 is a schematic view illustrating the configuration of a capturing part of a measurement device according to a second embodiment of the present disclosure.

FIG. 11 is a schematic view illustrating the configuration of a capturing part of a measurement device according to a third embodiment of the present disclosure.

FIG. 12 is a schematic view illustrating the configuration of a capturing part of a measurement device according to a fourth embodiment of the present disclosure.

FIG. 13 is a schematic view illustrating an aspect in which a heating mechanism is installed in a capturing part.

FIG. 14 is a schematic view illustrating the configuration of a droplet forming part of a measurement device according to a fifth embodiment of the present disclosure.

FIG. 15 is a schematic view illustrating the configuration of a measurement part of a measurement device according to a sixth embodiment of the present disclosure.

FIG. 16 is a schematic view illustrating the configuration of a measurement device according to a seventh embodiment of the present disclosure.

FIG. 17 is a schematic view illustrating an aspect in which a liquid feeding pump is added to the measurement device illustrated in FIG. 16.

FIG. 18 is a schematic view illustrating an aspect in which an aeration tank is used as the capturing part.

FIG. 19 is a schematic view illustrating the configuration of a measurement device according to an eighth embodiment of the present disclosure.

FIG. 20 is a schematic view illustrating a modification of a droplet forming part of the measurement device illustrated in FIG. 19.

FIG. 21 is a schematic view illustrating the configuration of a measurement device in the case where droplets are formed using an electrospray.

FIG. 22 is an enlarged pattern diagram illustrating a region of the electrospray in the measurement device illustrated in FIG. 21.

DETAILED DESCRIPTION

Embodiments of the present disclosure will now be described in detail. The present disclosure disclosed herein is not limited by the present embodiments. Respective embodiments may be appropriately combined unless a conflict arises in the processing content.

A measurement device according to one embodiment of the present disclosure includes: a droplet forming part configured to form aerosol-like liquid droplets from a liquid in which a fluorescent substance specifically bondable to detection target particles and a specimen are mixed with each other; a droplet sorting part configured to sort droplets having a diameter smaller than a predetermined value from the droplets formed by the droplet forming part; and a measurement part configured to irradiate light onto the droplets sorted by the droplet sorting part and configured to measure a fluorescence intensity of the droplets.

In the measurement device of the embodiment described above, the droplet sorting part may include a spray chamber configured to sort the droplets having a diameter smaller than a predetermined value using an inertial force. In this case, specifically, for example, the spray chamber is one selected from a group consisting of a cyclone-shaped spray chamber, a Scott-shaped spray chamber and an inertia branch-shaped spray chamber.

Furthermore, in the measurement device of the embodiment described above, the droplet sorting part is configured to sort droplets having a diameter of less than 20 µm.

Furthermore, in the measurement device of the embodiment described above, the measurement device may further include a capturing part configured to cause the liquid to capture detection target particles contained in a gas, cause a fluorescent substance, which is specifically bondable to the detection target particles, to be bonded to the detection target particles existing in the liquid, and supply the liquid in which the fluorescent substance and the detection target particles are mixed with each other, to the droplet forming part.

In some embodiments, in the measurement device of the embodiment described above, the droplet forming part may include a liquid accommodation part having a capacity of 0.1 ml to 5 ml and configured to accommodate the liquid in which the fluorescent substance specifically bondable to the detection target particles and the specimen are mixed with each other, a ring-shaped piezoelectric vibrator fitted to a lower end portion of the liquid accommodation part, and a mesh-like plate fixed to an inner side of a ring of the piezoelectric vibrator.

In some embodiments, in the measurement device of the embodiment described above, the droplet forming part may include a liquid accommodation part having a capacity of 0.1 ml to 5 ml and configured to accommodate the liquid in which the fluorescent substance specifically bondable to the detection target particles and the specimen are mixed with each other, a liquid flow path having a width of 1 mm or less and communicating with the liquid accommodation part, a gas flow path installed so as to merge with the liquid flow path in a tip portion of the liquid flow path, and a compressed gas introduction port configured to introduce a compressed gas into the gas flow path.

Furthermore, in the measurement device of the embodiment described above, the measurement part may be configured to measure the fluorescence intensity of the droplets in two or more kinds of different wavelength ranges.

Furthermore, in the measurement device of the embodiment described above, the measurement part may be configured to measure the fluorescence intensity of the droplets and the scattered light intensity of the droplets.

In the measurement device of the embodiment described above, specifically, for example, the fluorescent substance is a fluorescence-labeled antibody or a fluorescent sugar chain probe. The fluorescence-labeled antibody may have a property of changing the fluorescence intensity when specifically bonded. Alternatively, in the measurement device of the embodiment described above, the fluorescence-labeled antibody may have a property of allowing a plurality of fluorescent substances to gather together. In this case, the detection target particles modified with the fluorescence-labeled antibody are also aggregated. This makes it possible to obtain a more intense light emission.

Furthermore, a measurement method according to one embodiment of the present disclosure includes: a droplet forming step of forming aerosol-like liquid droplets from a liquid in which a fluorescent antibody specifically bondable to detection target particles and a specimen are mixed with each other; a droplet sorting step of sorting droplets having a diameter smaller than a predetermined value from the droplets formed at the droplet forming step; and a measurement step of irradiating light onto the droplets passed through the droplet sorting step and measuring the fluorescence intensity of the droplets.

In the measurement method of the embodiment described above, at the droplet sorting step, the droplets having a diameter smaller than a predetermined value may be sorted using an inertial force.

In the measurement method of the embodiment described above, at the droplet sorting step, droplets having a diameter less than 20 µm may be sorted.

In the measurement method of the embodiment described above, specifically, for example, the fluorescent substance is a fluorescence-labeled antibody or a fluorescent sugar chain probe. Alternatively, in the measurement method of the embodiment described above, the fluorescence-labeled antibody may have a property of allowing a plurality of fluorescent substances to gather together. In this case, the detection target particles modified with the fluorescence-labeled antibody are also aggregated. This makes it possible to obtain a more intense light emission.

Examples of the detection target particles contained in the gas include viruses, bacteria, pollen, toxic substances, etc. Examples of the detection target particles contained in the liquid include food which one does not want to ingest, an antibody to a particular disease, a small amount of protein such as cytokines, hormones or the like, a metabolite biomarker such as serotonin or the like. However, the detection target particles are not limited thereto as long as a fluorescent substance is specifically bondable to the detection target particles.

Next, specific examples of embodiments of the present disclosure will be described with reference to the accompanying drawings.

FIG. 1 is a schematic view illustrating the configuration of a measurement device according to a first embodiment of the present disclosure. In an example illustrated in FIG. 1, descriptions will be made by taking, as an example, a case where a measurement device 10 performs detection of detection target particles based on the fluorescence intensity of droplets. However, the present disclosure is not limited thereto. For example, the measurement device 10 may merely measure the fluorescence intensity of droplets. In this case, a user or another device may determine whether the detection target particles are contained in an inspection target gas, based on the fluorescence intensity measured by the measurement device 10.

As illustrated in FIG. 1, in the present embodiment, the measurement device 10 includes a dust removal part 11, a main pipe 18, a capturing part 12, a droplet forming part 13, a droplet sorting part 14, a measurement part 15, a liquid recovery part 16 and a suction pump 17.

The positional relationship of the respective parts will be briefly described. The main pipe 18 is a gas flow guide path. The dust removal part 11 is disposed at the upstream side of a gas flow guided by the main pipe 18. The suction pump 17, which is a gas flow forming mechanism configured to form a gas flow within the main pipe 18, is disposed at the downstream side of the gas flow guided by the main pipe 18. In other words, the suction pump 17 is configured to form a gas flow flowing from the dust removal part 11 toward the suction pump 17 within the main pipe 18. In some embodiments, as the gas flow forming mechanism, an air blower pump may be installed at the upstream side of the dust removal part 11. In this case, compressed air may be supplied from the air blower pump into the main pipe 18.

Furthermore, the droplet forming part 13, the droplet sorting part 14, the measurement part 15 and the liquid recovery part 16 are installed in the main pipe 18 between the dust removal part 11 and the suction pump 17 in the named order.

Next, descriptions will be made on the configurations of the respective parts. The dust removal part 11 has a gas flow resistance which is required to form aerosol-like droplets within the main pipe 18. The dust removal part 11 is configured to supply a clean gas by capturing particles which may affect the measurement.

Next, descriptions will be made on the capturing part 12. The capturing part 12 is configured to cause a liquid to capture detection target particles contained in an inspection target gas and is configured to cause a fluorescent substance, which is specifically bondable to the detection target particles, to be bonded to the detection target particles existing in the liquid.

In the present embodiment, as illustrated in FIG. 1, the capturing part 12 includes a cyclone 20 which is provided with a cyclone body 21, a gas introduction part 22 for introducing a gas into the cyclone body 21 and a liquid introduction part 23 for introducing a liquid into the cyclone body 21.

The cyclone body 21 has an inner surface (hereinafter referred to as a "wall surface") of a frusto-conical shape and is oriented so that a small-diameter-side end portion is positioned lower than a large-diameter-side end portion.

The gas introduction part 22 is installed in an upper portion of the cyclone body 21 so as to extend in a tangential direction of the wall surface of the cyclone body 21 and is gas-tightly connected to a coarse-dust removal part 19. The coarse-dust removal part 19 is configured to allow measurement target particles to pass therethrough and is configured to capture relatively-large particles. The gas introduced from the coarse-dust removal part 19 into the cyclone body 21 through the gas introduction part 22 is guided along the wall surface of the cyclone body 21 so as to swirl in a circumferential direction.

The liquid introduction part 23 includes a tank 23*a* configured to accommodate a liquid, a liquid introduction pipe 23*b* connected at one end to a lower portion of the tank 23*a* and connected at the other end to the wall surface of the cyclone body 21, and a flow rate control part 23*c* installed in the liquid introduction pipe 23*b*.

In the present embodiment, a liquid containing a fluorescent substance is accommodated within the tank 23*a*. The fluorescent substance is, for example, a fluorescence-labeled antibody. As illustrated in FIG. 2A, the fluorescence-labeled antibody Y is specifically bonded to a specific detection target particle P using an antibody-antigen reaction.

As illustrated in FIG. 2B, the fluorescent substance may be antibody agglomeration particles A whose surface is modified by a plurality of fluorescence-labeled antibodies Y. In this case, the fluorescence-labeled antibodies Y on surfaces of the antibody agglomeration particles A are specifically bonded to specific detection target particles P using an antibody-antigen reaction. Thus, it is possible to agglomerate the detection target particles P through the antibody agglomeration particle A. Accordingly, the volume intensity of the fluorescence-labeled antibodies Y increases, which makes it possible to increase the fluorescence intensity.

The other end of the liquid introduction pipe 23*b* is connected to the wall surface of the cyclone body 21 at a height position lower than the gas introduction part 22. On the other hand, the one end of the liquid introduction pipe 23*b* is disposed in a height position higher than the other end. If the flow rate control part 23*c* is opened, the liquid accommodated within the tank 23*a* is introduced into the cyclone body 21 through the liquid introduction pipe 23*b* using gravity.

However, the liquid introduction part 23 is not limited to this configuration. For example, the liquid introduction part 23 may include a syringe pump which accommodates a liquid containing a fluorescent substance. The tip of the syringe pump may be connected to the wall surface of the cyclone body 21. If the interior of the syringe pump is pressurized by a piston, the liquid containing the fluorescent substance may be introduced into the cyclone body 21.

In the present embodiment, a suction-exhaust part 24 configured to suction-exhaust and depressurize the interior of the cyclone body 21 and configured to introduce the gas from the gas introduction part 22 under a differential pressure so as to swirl in the circumferential direction, is installed above the cyclone body 21.

The suction-exhaust part 24 includes a suction-exhaust pipe 24*b* coaxially inserted into the upper portion of the cyclone body 21 and a suction-exhaust pump 24*a* installed in the suction-exhaust pipe 24*b*.

If the suction-exhaust pump 24*a* is operated, the interior of the cyclone body 21 is suction-exhausted and depressurized through the suction-exhaust pipe 24*b*. Under the differential pressure between the interior and exterior of the cyclone body 21, a gas existing outside the cyclone body 21 is drawn from the gas introduction part 22 into the cyclone body 21 through the coarse-dust removal part 19. Then, the gas introduced into the cyclone body 21 is guided along the wall surface of the cyclone body 21 and is moved downward while swirling in the circumferential direction. That is to say, the gas introduced into the cyclone body 21 forms a gas flow swirling in a spiral shape. At this time, the detection target particles existing in the gas are separated toward the wall surface of the cyclone body 21 under a centrifugal force because the detection target particles have a relatively-large specific gravity. On the other hand, the flow of a gas component having a relatively-small specific gravity is reversed in the lower portion of the cyclone body 21 due to the frusto-conical shape of the wall surface of the cyclone body 21, thereby forming an upward flow at the side of a center axis of the cyclone body 21. Then, the gas component having a relatively-small specific gravity is discharged outside through the suction-exhaust pipe 24*b*.

The liquid introduced from the liquid introduction part 23 into the cyclone body 21 is biased outward by the gas flow swirling in the circumferential direction and is formed into a film shape along the wall surface of the cyclone body 21.

In the present embodiment, a level detection part 25 configured to detect a level of the liquid formed into a film shape is installed in the wall surface of the cyclone body 21. The flow rate control part 23*c* of the liquid introduction part 23 is configured to control a flow rate based on a detection result of the level detection part 25.

More specifically, the level detection part 25 includes a pair of electrodes exposed toward the interior of the cyclone body 21 and a measuring part configured to measure the conductivity between the electrodes. If the level of the liquid is higher than the height position of the pair of electrodes, the electrodes are conducted through the liquid, whereby the conductivity grows relatively high. On the other hand, if the level of the liquid is lower than the height position of the pair of electrodes, the electrodes are insulated from each other, whereby the conductivity grows relatively low. A measurement result available in the case where the level of the liquid is higher than the height position of the pair of electrodes and a measurement result available in the case where the level of the liquid is lower than the height position of the pair of electrodes are obtained in advance by experiments. The value between the two measurement results is determined as a threshold value. Thereafter, if the measurement result of the measuring part is larger than the threshold value, it is determined that the level of the liquid is higher than the height position of the pair of electrodes. If the measurement result of the measuring part is smaller than the threshold value, it is determined that the level of the liquid is lower than the height position of the pair of electrodes.

If it is determined by the level detection part 25 that the level of the liquid is lower than the height position of the pair of electrodes, the flow rate control part 23c increases the flow rate of the liquid until the level of the liquid becomes higher than the height position of the pair of electrodes. This makes it possible to prevent a contact area of the liquid existing within the cyclone body 21 with respect to the gas from being reduced by the delivery or evaporation of the liquid.

A liquid supply pipe 26 is connected to the lower side of the cyclone body 21. A liquid feeding pump 27 is installed in the liquid supply pipe 26.

The interior of the cyclone body 21 is depressurized by the suction-exhaust part 24. However, by pressurizing and feeding the liquid existing within the liquid supply pipe 26 through the use of the liquid feeding pump 27, it is possible to continuously and stably supply the liquid from the interior of the cyclone body 21 toward the droplet forming part 13 through the liquid supply pipe 26.

Figure 13:
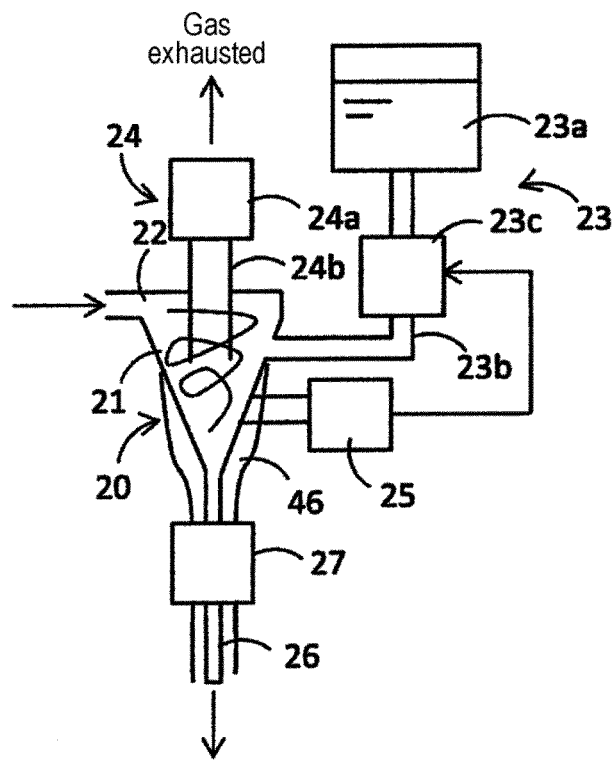

While not necessarily essential, as illustrated in FIG. 13, a heating mechanism 46 configured to heat the liquid may be installed in the capturing part 12. In this case, by heating the liquid close to, for example, body temperature (about 35 degrees C.) when the reactivity of the fluorescent substance is reduced in a low temperature environment such as a cold area or the like, it is possible to activate the fluorescent substance existing in the liquid and to increase the reaction speed.

In some embodiments, a cooling mechanism (not shown) configured to cool the liquid may be installed in the capturing part 12. In this case, by cooling the liquid close to, for example, body temperature (about 35 degrees C.) when the reactivity of the fluorescent substance is reduced in a high temperature environment such as a hot area or the like, it is possible to activate the fluorescent substance existing in the liquid and to increase the reaction speed.

Next, descriptions will be made on the droplet forming part 13. The droplet forming part 13 is to form aerosol-like droplets from the liquid supplied from the capturing part 12. More specifically, the droplet forming part 13 forms aerosol-like droplets from the liquid supplied from the capturing part 12 through the use of at least one of a nebulizer, an electrospray, a two-fluid nozzle, a piezoelectric element, an ultrasonic wave and a depressurization treatment.

In the present embodiment, as illustrated in FIG. 1, the droplet forming part 13 includes a throttle portion 18a where the diameter of the main pipe 18 is significantly reduced. An end portion of the liquid supply pipe 26 is coaxially inserted into the throttle portion 18a. When the gas flow flowing in the main pipe 18 passes through the throttle portion 18a, the velocity of the gas flow increases. At this time, a negative pressure is generated in the end portion of the liquid supply pipe 26 by the high-velocity gas flow passing through the throttle portion 18a. The liquid existing within the liquid supply pipe 26 is sucked and split by the negative pressure. Thus, aerosol-like droplets are formed from the liquid supplied from the liquid supply pipe 26 (two-fluid nozzle).

Figure 3:
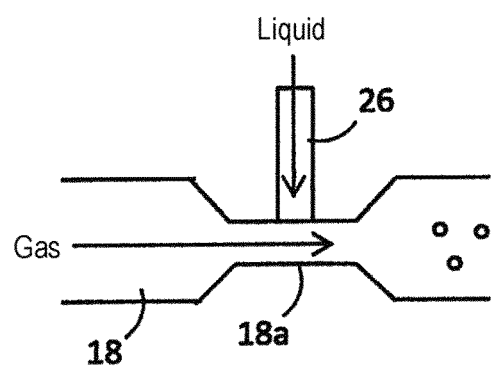

While in the example illustrated in FIG. 1, the end portion of the liquid supply pipe 26 has been described to be coaxially inserted into the throttle portion 18a, the present disclosure is not limited thereto. For example, as illustrated in FIG. 3, the end portion of the liquid supply pipe 26 may be connected to the throttle portion 18a at a right angle with respect to the throttle portion 18a.

Next, descriptions will be made on the droplet sorting part 14. The droplet sorting part 14 is to sort droplets having a diameter smaller than a predetermined value, among the droplets supplied from the droplet forming part 13.

As the droplet sorting part 14, it may be possible to use, for example, a spray chamber configured to sort droplets having a diameter smaller than a predetermined value through the use of an inertial force. Specifically, for example, the droplet sorting part 14 may be one selected from a group consisting of a cyclone-shaped spray chamber, a Scott-shaped spray chamber and an inertial branch-shaped spray chamber. Such a spray chamber is well-known in the technical field of inductively coupled plasma (ICP) emission spectrometry and is illustrated in, for example, JIS K0133. However, in the present embodiment, there is not provided an effect that the droplets having a diameter decomposable by inductively-coupled plasma are sorted using a spray chamber. As will be described later, by combining a spray chamber with a method which makes use of a fluorescent substance specifically bondable to detection target particles, the present embodiment provides an effect unexpected from the conventional spray chamber in that detection target particles can be accurately detected by increasing the difference between the fluorescence intensity of droplets not containing detection target particles and the fluorescence intensity of droplets containing detection target particles.

Figure 4:
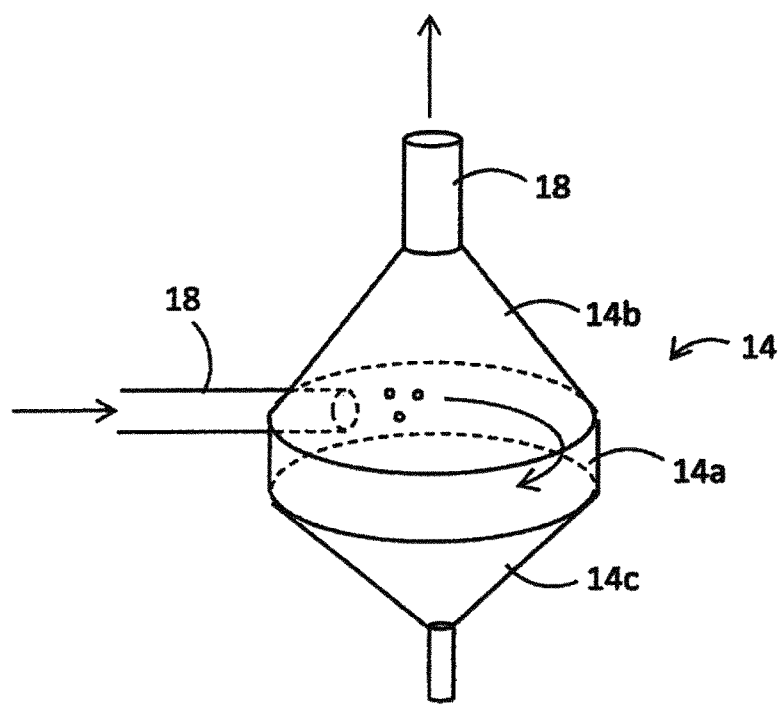

FIG. 4 is a schematic view illustrating one example of the configuration of the droplet sorting part 14. The droplet sorting part 14 illustrated in FIG. 4 is a cyclone-shaped spray chamber. The droplet sorting part 14 includes a central chamber body 14a having a cylindrical inner surface, an upper chamber body 14b having a frusto-conical inner surface formed in a central upper end portion, and a lower chamber body 14c having a frusto-conical inner surface formed in a central lower end portion.

The main pipe 18 is connected to the inner surface of the central chamber body 14a in such an orientation as to extend in a tangential direction of the inner surface. The gas flow containing droplets introduced into the central chamber body 14a through the main pipe 18 is guided along the inner surface of the central chamber body 14a under an inertial force and is caused to swirl in a circumferential direction. At this time, the droplets having a diameter equal to or larger than a predetermined value are separated toward the inner surface of the central chamber body 14a under a centrifugal force, so that the droplets impinge against and adhere to the inner surface. Thus, the droplets having a diameter equal to or larger than a predetermined value are removed from the gas flow. The droplets having a diameter smaller than the predetermined value are carried by the gas flow and are supplied from the upper side of the upper chamber body 14*b* toward the measurement part 15. In the meantime, the droplets (liquid) adhering to the inner surface of the central chamber body 14*a* are allowed to flow down toward the lower chamber body 14*c* using gravity and are discharged outside from the lower side of the lower chamber body 14*c*. In the case where a small amount of droplets (liquid) adheres to the inner surface of the central chamber body 14*a*, they are evaporated. Thus, there is no need to install a liquid discharge mechanism.

In this regard, the spray chamber sorts the droplets through the use of an inertial force. Thus, the upper limit value of the diameter of the droplets sorted by the spray chamber has a correlation with mechanical parameters such as the dimension and shape of the spray chamber, the flow velocity of the gas flow, and the like. Accordingly, by appropriately selecting the mechanical parameters such as the dimension and shape of the spray chamber, the flow velocity of the gas flow, and the like, it is possible to set the upper limit value of the diameter of the droplets sorted by the spray chamber at a desired value. The diameter of the droplets sorted by the spray chamber may be appropriately selected depending on a measurement target or a measurement purpose. In the case where viruses or bacteria are used as the measurement target, the diameter of the droplets sorted by the spray chamber may be 50 μm or less, specifically 20 μm or less.

Next, descriptions will be made on the measurement part 15. FIG. 5 is a schematic view illustrating one example of the configuration of the measurement part 15. The measurement part 15 is to irradiate light onto the droplets and measure the fluorescence intensity of the droplets.

In the present embodiment, as illustrated in FIG. 5, the measurement part 15 includes a case body 56 of, for example, a square shape, which is connected to the main pipe 18 and which defines a flow space of the gas flow containing the droplets sorted by the droplet sorting part 14. Light transmission windows 52*a* and 52*b* parallel to each other and made of quartz are disposed in the mutually-opposing upper and lower (or left and right) surfaces of the case body 56.

At the outer side of one light transmission window 52*a*, there is installed a light-emitting part 51 which irradiates laser light having a wavelength deviated from a wavelength of fluorescent light emitted from the fluorescent substance into the case body 56. Furthermore, at the outer side of the other light transmission window 52*b*, there is installed an optical filter 53 which blocks the light having a wavelength deviated from a wavelength of fluorescent light emitted from the fluorescent substance. At the further outer side of the other light transmission window 52*b*, there is installed a light-receiving part 54 which receives the fluorescent light of the fluorescent substance and converts the same to an electrical signal. The light-receiving part 54 is, for example, a photomultiplier tube. The light-receiving part 54 is configured to output, for example, an electric current of a signal level corresponding to the intensity of the light received from the optical filter 53, to a light reception output measuring part 55.

The light reception output measuring part 55 is configured to, for example, convert a current to a voltage, compare a voltage signal Ia indicating the converted voltage with a predetermined threshold value Is, and notify or display on a display part (not shown) an arm indicating the detection of detection target particles when it is determined that the voltage signal Ia is larger than the threshold value Is.

In this regard, the voltage signal Ia is a signal corresponding to the light reception intensity. Thus, the threshold value Is is determined as follows. That is to say, the threshold value Is is set at a value between a fluorescence intensity available when the droplets formed by the droplet forming part 13 pass through the case body 56 in the case where detection target particles do not exist in an inspection target gas and a fluorescence intensity available when the droplets formed by the droplet forming part 13 pass through the case body 56 in a state in which detection target particles are contained in an inspection target gas and in which a fluorescent substance is bonded to the detection target particles. The fluorescence intensity available when the detection target particles do not exist in the inspection target gas corresponds to the intensity of the fluorescent light emitted from the fluorescent substance adhering to the dust contained in the gas passing through the case body 56 or the fluorescent substance contained in the droplets not containing the detection target particles. The fluorescent substance is specifically bonded to the detection target particles. As a result, generally speaking, the density of the fluorescent light available when the detection target particles exist is higher than the density of the fluorescent light available when the detection target particles do not exist. Thus, a difference in the fluorescence intensity corresponding to the existence or absence of the detection target particles is generated.

Referring back to FIG. 1, a liquid recovery part 16 composed of, for example, a mesh body and configured to capture the droplets passed through the measurement part 15 is installed at the downstream side of the measurement part 15. A suction pump 17 is installed at the downstream side of the liquid recovery part 16. The gas passed through the liquid recovery part 16 is exhausted outside the measurement device 10 via, for example, a filter (not shown) for adsorbing and removing the detection target particles. A liquid discharge mechanism is installed in the liquid recovery part 16. However, if the amount of droplets (liquid) passing through the liquid recovery part 16 is sufficiently small, the droplets (liquid) are evaporated. Thus, there is no need to install the liquid discharge mechanism.

Next, descriptions will be made on a process in which the droplets having a diameter smaller than a predetermined value are sorted by the droplet sorting part 14.

In the method which makes use of the fluorescent substance specifically bonded to the detection target particles, an unreacted fluorescent substance becomes noise. FIG. 6 is a schematic diagram for explaining the fluorescence intensity in the case where the diameter of the droplets is relatively large. In an example illustrated in FIG. 6, the shade of a color indicates the strength of the fluorescence intensity.

As can be noted from the liquid droplet designated by reference numeral 301 in FIG. 6, the fluorescent substance existing in the liquid droplet emits fluorescent light even if the fluorescent substance is not bonded to the detection target particles. Furthermore, as can be noted from the liquid droplet designated by reference numeral 302, if the fluorescent substance existing in the liquid droplet is specifically bonded to the detection target particles to be detected, the volume density of the fluorescent substance increases. Thus, the fluorescence intensity grows higher as compared with a case where the fluorescent substance is not bonded to the detection target particles. In the liquid droplet designated by reference numeral 302 in FIG. 6, a portion of the liquid droplet 302 designated by reference numeral 303 indicates the portion containing the fluorescent substance not bonded to the detection target particles. Another portion of the liquid droplet 302 designated by reference numeral 304 indicates the portion containing the fluorescent substance bonded to the detection target particles.

Figure 6:
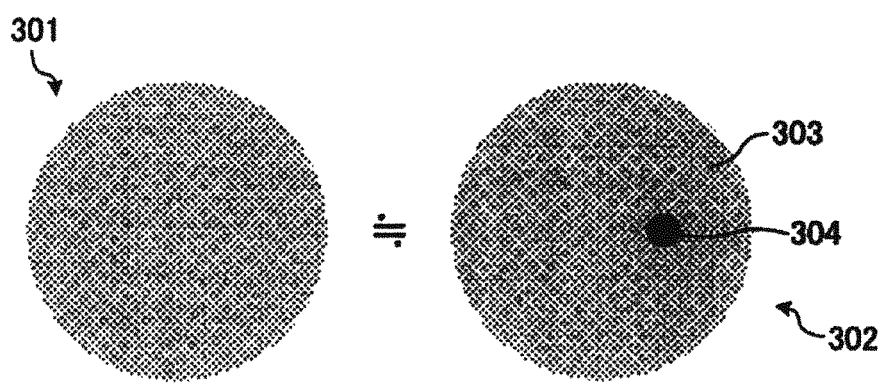

As illustrated in FIG. 6, if the diameter of the liquid droplet is relatively large, there may be a case where, due to the fluorescent light emitted from the fluorescent substance not bonded to the detection target particles to be detected, it is not possible to distinguish the difference between the fluorescence intensity of the liquid droplet designated by reference numeral 301 and the fluorescence intensity of the liquid droplet designated by reference numeral 302. In other words, there may be a case where the fluorescence intensities of the whole droplets are equal to each other, which makes it difficult to measure the difference in the fluorescence intensity. In this case, it is not possible to detect the detection target particles to be detected.

Thus, according to the present embodiment, the droplets having a diameter smaller than a predetermined value are sorted by the droplet sorting part 14. For that reason, even if an unreacted fluorescent substance is not removed from the liquid prior to forming the droplets, it is possible to accurately measure the fluorescent light emitted from the fluorescent substance bonded to the detection target particles. The improvement of the measurement accuracy improves the detection accuracy of the detection target particles. Furthermore, it is possible to detect the detection target particles in real time. For example, it is possible to accurately detect viruses or bacteria in real time.

In the related art, there is a problem in that the fluorescent light emitted from the unreacted fluorescent substance is measured as mentioned above so that the measurement accuracy is poor. Under the circumstances, a method of measuring the fluorescence intensity of droplets after separating an unreacted fluorescent substance from a liquid prior to forming droplets has been considered. However, this method is time-consuming and has a difficulty in continuously measuring the fluorescence intensity. In contrast, according to the present embodiment, even if an unreacted fluorescent substance is not removed from a liquid prior to forming droplets, it is possible to continuously and easily measure the fluorescence intensity.

On the other hand, in the fluorescence correlation spectroscopy, by focusing the laser, it is possible to reduce the volume of a liquid to be measured from femtoliters (fL) up to sub-femtoliters (fL). In a system using the fluorescence correlation spectroscopy, if the volume of the liquid to be measured is reduced from femtoliters (fL) up to sub-femtoliters (fL), even when an unreacted fluorescent substance is not removed, it is possible to measure the detection target particles to be detected.

In view of this, it is preferred that the droplet sorting part 14 reduces the diameter of the droplets to be measured by the measurement part 15. Specifically, it is desirable for the droplet sorting part 14 to sort the droplets so that 50% or more of the droplets have a diameter of 20 μm or less. In this case, even when an unreacted fluorescent substance is not removed, it is possible for the measurement part 15 to accurately measure the detection target particles to be detected.

Figure 7:
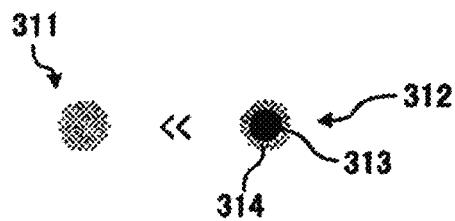

FIG. 7 is a view illustrating the fluorescence intensity in the case where the diameter of the droplets is relatively small. In an example illustrated in FIG. 7, there are illustrated, by way of example, a case where a liquid droplet designated by reference numeral 311 does not contain a fluorescent substance bonded to the detection target particles to be detected and a case where a liquid droplet designated by reference numeral 312 contains a fluorescent substance bonded to the detection target particles in the portion designated by reference numeral 313. In addition, there is illustrated, by way of example, a case where a fluorescent substance not bonded to the detection target particles exists in the portion of the liquid droplet 312 designated by reference numeral 314.

As can be noted from the liquid droplet designated by reference numeral 311 and the liquid droplet designated by reference numeral 312 in FIG. 7, if the diameter of the droplets is reduced, the difference between the fluorescence intensity of the droplets not containing the detection target particles and the fluorescence intensity of the droplets containing the detection target particles grows larger. This makes it possible to accurately detect the detection target particles to be detected.

It is difficult to further reduce the diameter of the laser. In the fluorescence correlation spectroscopy, it is difficult to make the volume of the liquid to be measured smaller than sub-femtoliters. Similarly, in the measurement part 15, it is difficult to reduce the diameter of the light irradiated by the light-emitting part 51. In other words, there is a limit in reducing the amount of the liquid measured at a time by reducing the diameter of the laser.

In contrast, according to the present embodiment, even if the diameter of the laser is not reduced, it is possible to reduce the volume of the liquid measured at a time and to enhance the measurement sensitivity by further reducing the diameter of the droplets sorted by the droplet sorting part 14. Furthermore, it is possible to use a low-priced laser without having to use a special laser. Since a configuration for reducing the diameter of the laser is not needed, it is possible to simplify a device configuration.

Next, an operation of the present embodiment configured as above (a measurement method according to one embodiment of the present disclosure) will be described.

First, as illustrated in FIG. 1, a gas (e.g., an air) is drawn into the main pipe 18 via the dust removal part 11 by the suction pump 17. Thus, a gas flow sequentially flowing through the droplet forming part 13, the droplet sorting part 14, the measurement part 15 and the liquid recovery part 16 is formed and is exhausted via the suction pump 17 and the filter (not shown).

In addition, with the operation of the suction-exhaust pump 24a of the capturing part 12, a gas (e.g., an air) is drawn into the gas introduction part 22 of the capturing part 12 via the coarse-dust removal part 19 and is introduced from the gas introduction part 22 into the cyclone body 21. Moreover, a liquid containing a fluorescent substance is introduced from the liquid introduction part 23 into the cyclone body 21.

The gas introduced from the gas introduction part 22 into the cyclone body 21 is guided along the wall surface of the cyclone body 21 and is swirled in the circumferential direction, thereby forming a spiral gas flow within the cyclone body 21. The liquid introduced from the liquid introduction part 23 into the cyclone body 21 is biased radially outward by the spiral gas flow and is formed into a film shape along the wall surface of the cyclone body 21.

The detection target particles contained in the gas are separated toward the wall surface of the cyclone body 21 under a centrifugal force and are captured in the liquid formed into a film shape. The fluorescent substance contained in the liquid is specifically bonded to the detection target particles thus captured. Further, depending on the fluorescent substance, there may be a case where some time is required in causing the fluorescent substance to be bonded to the detection target particles. In the present embodiment, a reaction is generated within the cyclone. Thus, it is possible to bond the fluorescent substance to the detection target particles more reliably than a method in which a fluorescent substance is bonded to detection target particles within a flow path. In addition, the liquid existing within the cyclone may be set to stay for an arbitrary amount of time.

The liquid that has captured the detection target particles on the wall surface of the cyclone body 21 gradually flows downward using gravity. Then, with the operation of the liquid feeding pump 27, the liquid is continuously supplied from the lower side of the cyclone body 21 toward the droplet forming part 13 via the liquid supply pipe 26.

In the droplet forming part 13, the liquid supplied from the capturing part 12 is drawn out from the end portion of the liquid supply pipe 26 by the high-velocity gas flow passing through the throttle portion 18a of the main pipe 18 so that aerosol-like droplets are formed. The aerosol-like droplets thus formed are carried by the gas flow in the main pipe 18 and are supplied to the droplet sorting part 14.

As illustrated in FIG. 4, in the droplet sorting part 14, the gas flow containing the droplets supplied from the droplet forming part 13 is guided along the cylindrical inner surface of the central chamber body 14a and is swirled in the circumferential direction. At this time, the droplets having a diameter equal to or larger than a predetermined value, which are contained in the gas flow, are separated toward the inner surface of the central chamber body 14a under a centrifugal force. The droplets impinge against and adhere to the inner surface. On the other hand, the droplets having a diameter smaller than the predetermined value are moved upward while swirling in the circumferential direction together with the gas flow and are supplied from the upper side of the upper chamber body 14b toward the measurement part 15.

Figure 5:
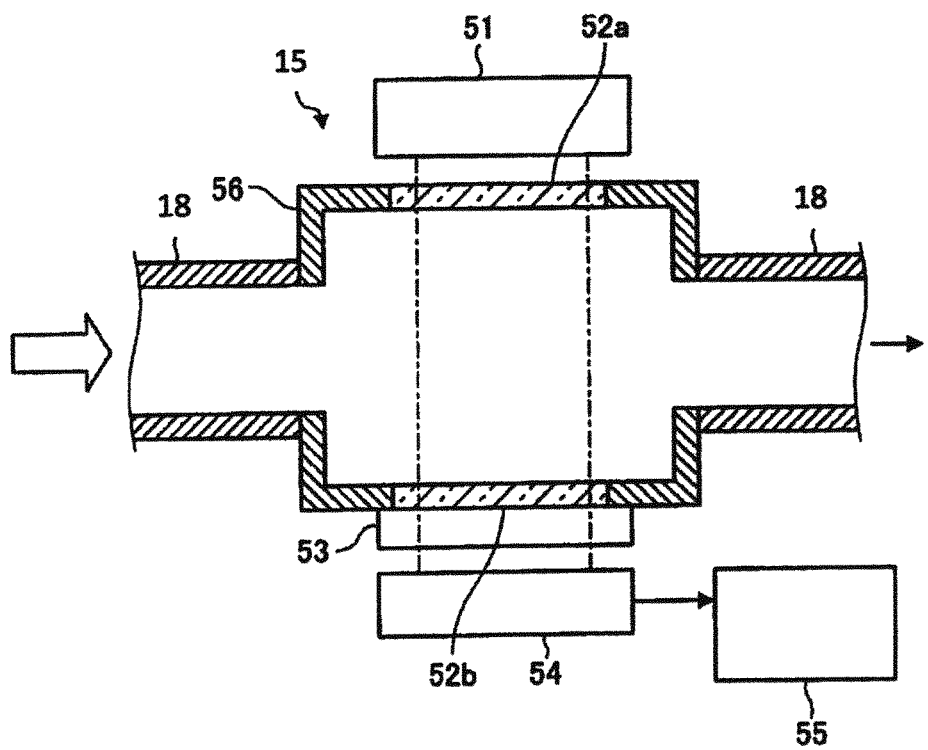

As illustrated in FIG. 5, the measurement part 15 irradiates light onto the droplets sorted by the droplet sorting part 14 and measures the fluorescence intensity of the droplets irradiated by the light. Specifically, the light is irradiated onto the droplets guided through the main pipe 18 and the fluorescence intensity is measured. Thereafter, for example, the measurement part 15 compares the measured fluorescence intensity with a threshold value to determine whether the detection target particles are contained in the inspection target gas. In other words, the measurement part 15 detects the detection target particles from the inspection target gas.

For example, in the measurement part 15, the light-emitting part 51 irradiates ultraviolet laser light into the case body 56 through which the droplets pass. Thus, the fluorescent substance existing in the droplets is excited by the ultraviolet laser light to emit fluorescent light. Thereafter, the ultraviolet laser light is blocked by the optical filter 53. Light having a fluorescence wavelength is selectively detected by the light-receiving part 54. The intensity of the light detected by the light-receiving part 54 is proportional to the volume density of the fluorescent substance existing in the droplets formed by the droplet forming part 13.

If the detection target particles exist in the droplets formed by the droplet forming part 13, the intensity of the light detected by the light-receiving part 54 becomes larger than the threshold value Is. Thus, an alarm of detection of the detection target particles is generated by the light reception output measuring part 55.

Furthermore, if the detection target particles do not exist in the droplets formed by the droplet forming part 13, even when fine dust existing in the air gets into the droplets formed by the droplet forming part 13 and the fluorescent substance adheres to the dust, the density of the fluorescent substance is much smaller than the density of the fluorescent substance bonded to the detection target particles. Thus, the light reception intensity detected by the light receiving part 54 is smaller than the predetermined threshold value Is.

The droplets passed through the measurement part 15 are separated into a gas and a liquid by the liquid recovery part 16 where the liquid is recovered. On the other hand, the gas is exhausted outside the measurement device 10 by the suction pump 17 installed at the downstream side of the liquid recovery part 16.

Next, specific examples will be described.

Figure 8:
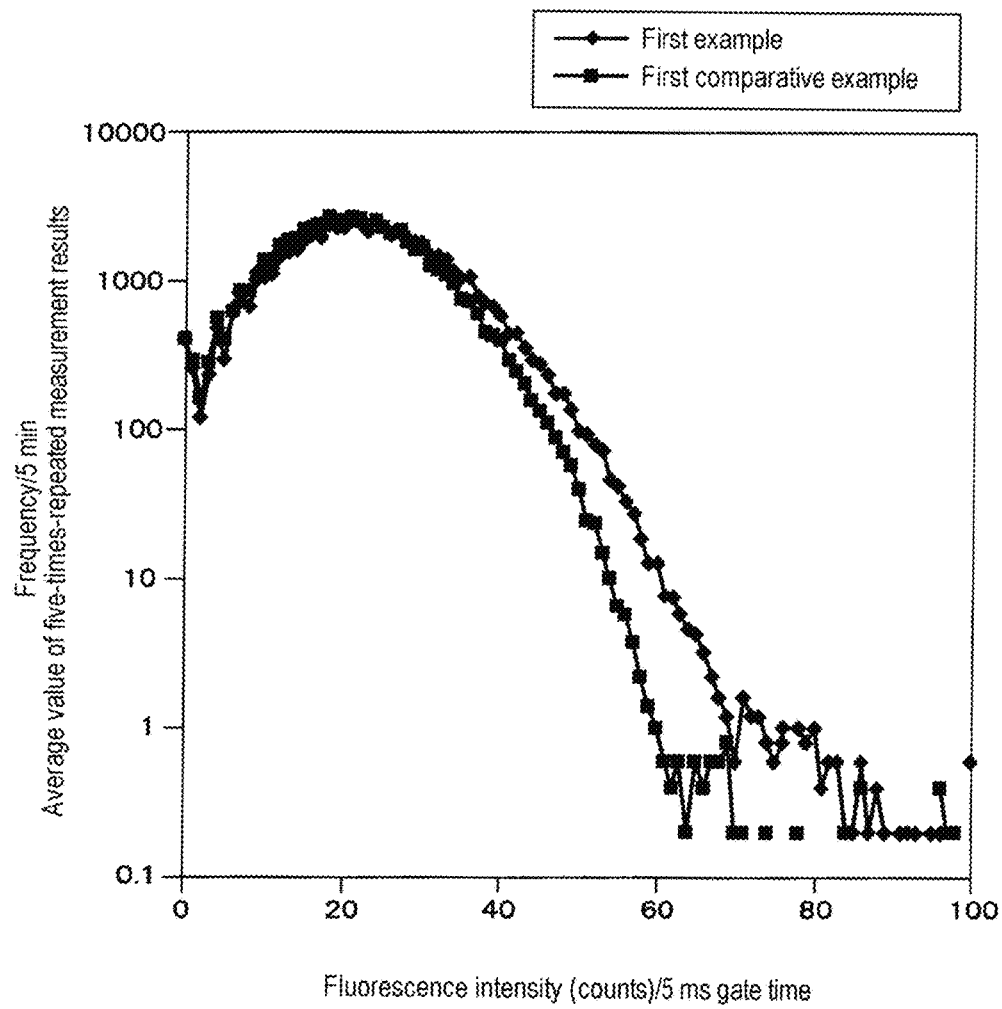

In a first example of the present embodiment, aerosol-like droplets were formed by the droplet forming part 13 while supplying, at a flow rate of 0.1 ml/hr, a liquid obtained by $5 \times 10^5$ times diluting a reagent which contains detection target particles (antigens) and antibodies labeled with fluorescent dye PE-Cy5 (the concentration of the detection target particles in the liquid: $3 \times 10^7$ pieces/ml=0.002 ng/ml). The droplets having a diameter smaller than a predetermined value were sorted by the droplet sorting part 14. Thereafter, the fluorescence intensity of the droplets was measured by the measurement part 15 in terms of the number of photons detected by the light-receiving part 54 for a gate time of 5 ms. The measurement result of the first example is indicated by rhombic dots in FIG. 8. In FIG. 8, the horizontal axis indicates the number of photons detected by the light-receiving part 54 for the gate time of 5 ms, namely the fluorescence intensity of the droplets. The vertical axis indicates the average value of five-times-repeated measurement results of the number of detection times (detection frequency) of the droplets emitting the fluorescent light of such fluorescence intensity, for a period of time of 5 minutes.

In a first comparative example, the fluorescence intensity of droplets was measured in the same method as the first example except that a liquid not containing detection target particles and containing only fluorescence-labeled antibodies is supplied to the droplet forming part 13. The measurement result of the first comparative example is indicated by square dots in FIG. 8.

As illustrated in FIG. 8, the measurement result of the first example is distinguishable from the measurement result of the first comparative example. That is to say, it was confirmed that the detection target particles can be detected at high sensitivity in the present embodiment. Particularly, in the first example, the detection sensitivity of 0.002 ng/ml was achieved. The detection sensitivity is significantly higher than the standard sensitivity (0.5 ng/ml to 10 ng/ml) available when noroviruses are detected using the current EIA method or the immune-chromatography method.

Next, in a second example of the present embodiment, the fluorescence intensity of droplets was measured in the same method as the first example except that a liquid obtained by $5 \times 10^3$ times diluting the reagent used in the first example (the concentration of the detection target particles in the liquid: 0.2 ng/ml) is supplied to the droplet forming part 13.

Furthermore, in a second comparative example, the fluorescence intensity of droplets was measured in the same method as the second example except that aerosol-like droplets formed by the droplet forming part 13 are directly supplied to the measurement part 15 without using the droplet sorting part 14.

Figure 9:
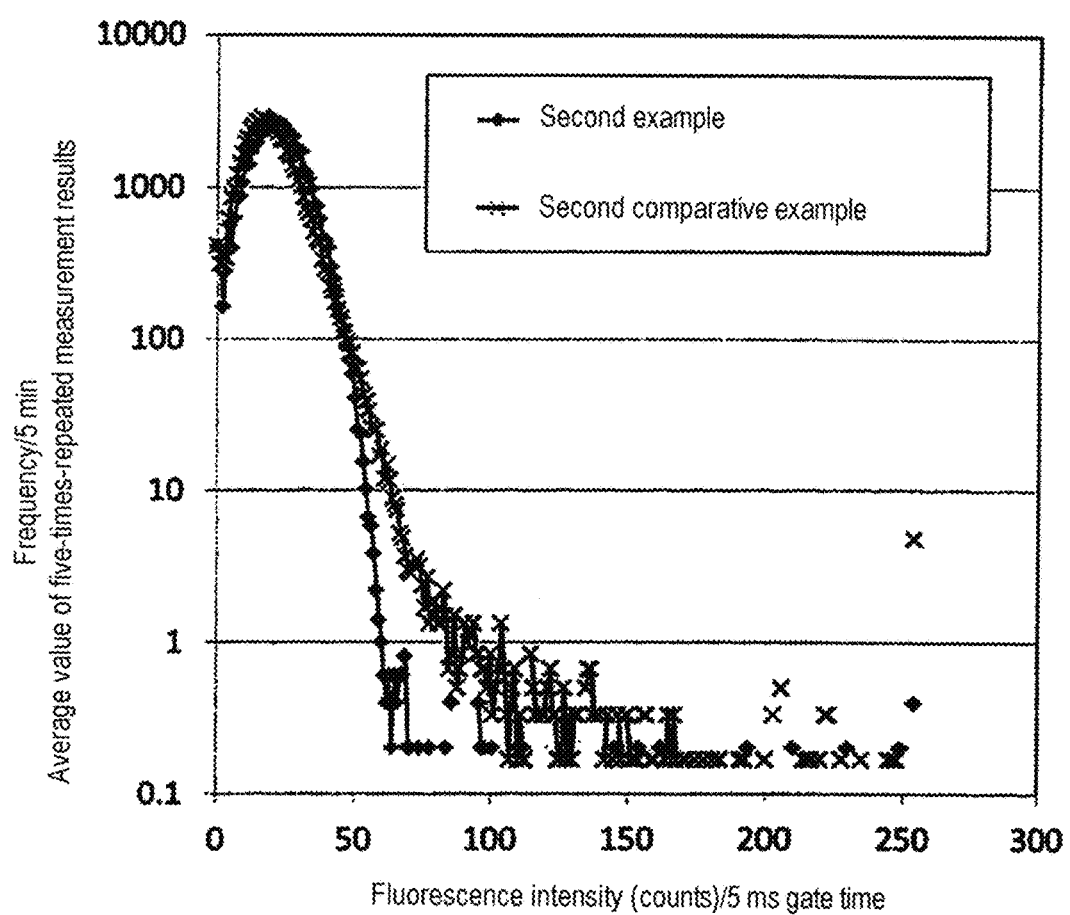

The measurement result of the second example and the measurement result of the second comparative example are overlappingly illustrated in FIG. 9. In FIG. 9, the round mark dots indicate the measurement result of the second example. The X mark dots indicate the measurement result of the second comparative example.

As illustrated in FIG. 9, in the measurement result of the second example using the droplet sorting part 14, as compared with the measurement result of the second comparative example not using the droplet sorting part 14, the detection frequency of the relatively large droplets corresponding to the number of photons of 60 or more is significantly reduced. However, the detection frequency of the relatively small droplets corresponding to the number of photons of less than 60 is not reduced. That is to say, it can be noted that the relatively small droplets corresponding to the number of photons of less than 60 are sorted. Accordingly, it was confirmed that, by using the droplet sorting part 14, it is possible to effectively sort the droplets having a relatively small diameter.

According to the present embodiment described above, the droplets having a diameter smaller than a predetermined value are sorted by the droplet sorting part 14. Thus, the difference between the fluorescence intensity of the droplets containing the detection target particles and the fluorescence intensity of the droplets not containing the detection target particles grows larger. This makes it possible to significantly improve the detection accuracy of the detection target particles.

Further, according to the present embodiment described above, in the capturing part 12, the inspection target gas is introduced into the cyclone 20. Thus, as compared with a method in which the inspection target gas is introduced into a fluid chip having a micro-size as described in Patent Document 1, it is possible to significantly increase the gas introduction amount per unit time. Furthermore, the liquid introduced into the cyclone 20 is formed into a film shape along the wall surface of the cyclone body 21. Thus, the contact area of the liquid with respect to the inspection target gas increases. Moreover, the detection target particles existing in the gas are separated toward the wall surface of the cyclone body 21 under a centrifugal force. Thus, it is possible to effectively bring the detection target particles into contact with the liquid. Owing to these actions, it is possible to significantly enhance the capturing efficiency of the detection target particles of the gas in the liquid and to significantly improve the detection accuracy of the detection target particles.

Furthermore, according to the present embodiment, in the cyclone 20, the liquid formed into a film shape is not only fed by the liquid feeding pump 27 but also continuously evaporated by a swirling gas. However, the introduction amount of the liquid is adjusted based on the detection result of the level detection part 25. It is therefore possible to prevent the level of the liquid from being lowered. That is to say, it is possible to prevent the contact area of the liquid with respect to the inspection target gas from being reduced. Accordingly, it is possible to prevent reduction of the capturing efficiency of the detection target particles and to prevent reduction of the detection accuracy.

Furthermore, according to the present embodiment, the suction-exhaust part 24 configured to suction-exhaust and depressurize the interior of the cyclone 20 and configured to introduce the gas from the gas introduction part of the cyclone 20 under a differential pressure so as to swirl in the circumferential direction, is installed above the cyclone 20. It is therefore possible to swirl the gas with a simple structure Furthermore, in the first embodiment, as illustrated in FIG. 1, the gas which forms the gas flow in the main pipe 18 and the gas which makes contact with the liquid in the capturing part 12 are supplied from mutually-different systems through the dust removal part 11 or the coarse-dust removal part 19. However, the present disclosure is not limited thereto. A branch pipe branched from the main pipe 18 at a position between the dust removal part 11 and the droplet forming part 13 may be gas-tightly connected to the gas introduction part 22 of the capturing part 12. A gas may be supplied to the capturing part 12 from the same system as the supply system of the gas which forms the gas flow in the main pipe 18. In the case where the gas is supplied to the capturing part 12 from a pipe differing from the main pipe 18 as illustrated in FIG. 1, a clean gas (e.g., an inert gas such as a nitrogen gas or the like) may be supplied to the main pipe 18.

Furthermore, in the first embodiment, the gas which makes contact with the liquid in the capturing part 12 may be ambient air or may be the breath of a human. In the case where the breath of a human is used, for example, one end of the pipe connected to the gas introduction part 22 may be expanded in a trumpet-like shape and the breath of a human may be introduced by bringing a mouth close to a portion expanded in a trumpet-like shape.

Figure 10:
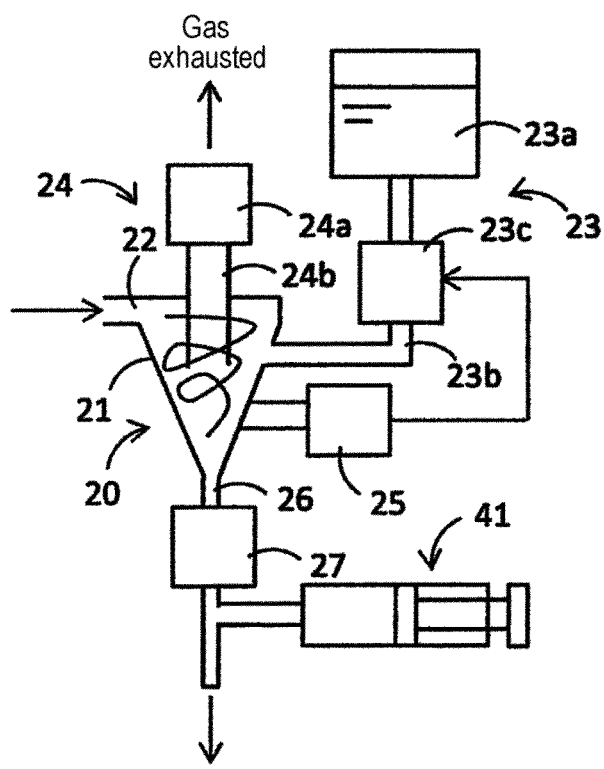

Furthermore, in the first embodiment, as illustrated in FIG. 1, the liquid introduction part 23 is configured to introduce the liquid containing the fluorescent substance into the cyclone body 21. However, the present disclosure is not limited thereto. As illustrated in FIG. 10, a second liquid introduction part 41 configured to merge the liquid containing the fluorescent substance with the liquid flowing through the liquid supply pipe 26 may be connected to the liquid supply pipe 26 which interconnects the lower portion of the cyclone 20 and the droplet forming part 13 (a second embodiment). In this case, for example, the liquid introduction part 23 may introduce water into the cyclone body 21.

In the illustrated example, the second liquid introduction part 41 includes a syringe pump which accommodates a liquid containing a fluorescent substance. The tip of the syringe pump is gas-tightly connected to the liquid supply pipe 26. If the interior of the syringe pump is pressurized by a piston, the liquid containing the fluorescent substance is merged with the liquid flowing through the liquid supply pipe 26.

In the case where the second liquid introduction part 41 is installed in the liquid supply pipe 26 as described above, the liquid introduction part 23 installed in the cyclone 20 may be configured to introduce the liquid for pretreating the detection target particles into the cyclone body 21. The pretreatment refers to, for example, a destruction process of outer membranes of the detection target particles, a surface wax removal process, or the like.

Specifically, for example, in the case of using a fluorescent substance specifically bonded to the internal structures of the detection target particles, a liquid (e.g., an alkali liquid or a liquid having a low osmotic pressure) which destroys the outer membrane structures of the detection target particles (e.g., cell membranes of bacteria) and exposes the internal structures to the liquid is introduced from the liquid introduction part 23 into the cyclone body 21. It is therefore possible to detect the detection target particles by allowing the fluorescent substance of the liquid merged from the second liquid introduction part 41 in the liquid supply pipe 26 to be bonded to the internal structures of the detection target particles.

Figure 11:
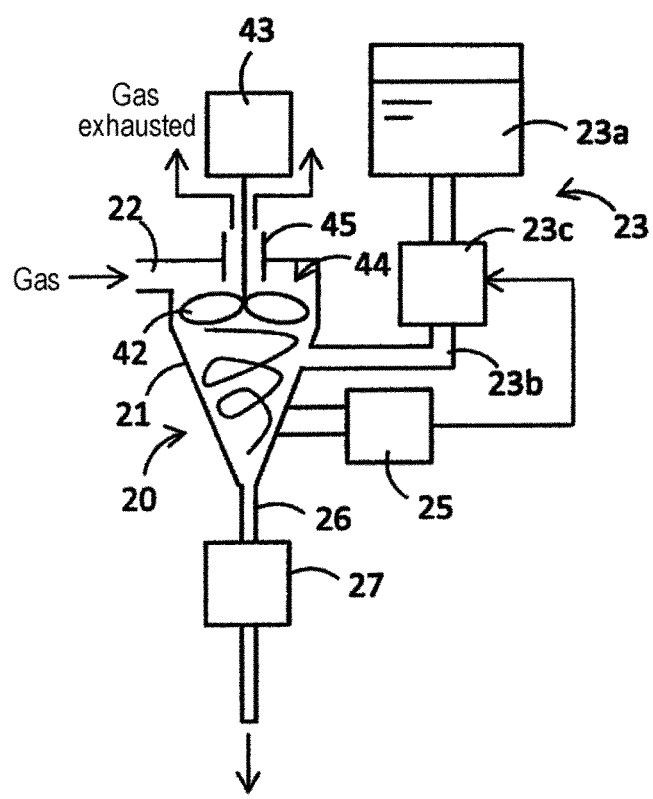

Furthermore, in the first embodiment, in order to form a gas flow swirling in the circumferential direction within the cyclone body 21, as illustrated in FIG. 1, the suction-exhaust part 24 is installed above the cyclone 20. However, the present disclosure is not limited thereto. As illustrated in FIG. 11, a swirling part 44 configured to swirl the gas introduced from the gas introduction part 22 of the cyclone 20 in the circumferential direction may be installed within the cyclone 20 (a third embodiment).

In the illustrated example, the swirling part 44 includes an impeller (propeller) 42 axially disposed within the cyclone body 21, and a rotational drive part 43 (e.g., a motor) configured to supply rotational drive power to the impeller 42. An exhaust hole 45 is coaxially formed in the upper portion of the cyclone body 21. A rotary shaft of the rotational drive part 43 is connected to the impeller 42 through the exhaust hole 45.

If the impeller 42 is rotated by the rotational drive power supplied from the rotational drive part 43, the gas existing within the cyclone body 21 is biased and pressed by blades of the impeller 42 so as to swirl in the circumferential direction, whereby a spiral gas flow is formed within the cyclone body 21. At this time, the detection target particles existing in the gas are separated toward the wall surface of the cyclone body 21 under a centrifugal force because the detection target particles have a relatively large specific gravity. On the other hand, the flow of a gas component having a relatively-small specific gravity is reversed in the lower portion of the cyclone body 21 due to the frusto-conical shape of the wall surface of the cyclone body 21, thereby forming an upward flow at the side of a center axis of the cyclone body 21. Then, the gas component having a relatively-small specific gravity is discharged outside through the exhaust hole 45.

The liquid introduced from the liquid introduction part 23 into the cyclone body 21 is biased radially outward by the spiral gas flow and is formed into a film shape. Then, the detection target particles separated toward the wall surface of the cyclone body 21 under a centrifugal force are captured in the liquid formed into a film shape.

According to the third embodiment described above, the interior of the cyclone body 21 has a positive pressure. Thus, it is easy to feed the liquid from the cyclone body 21 to the droplet forming part 13 and it is possible to omit the liquid feeding pump 27. In addition, according to this embodiment, the mechanism for swirling the gas is installed within the cyclone 20. This makes it easy to reduce the size of the cyclone 20.

Figure 12:
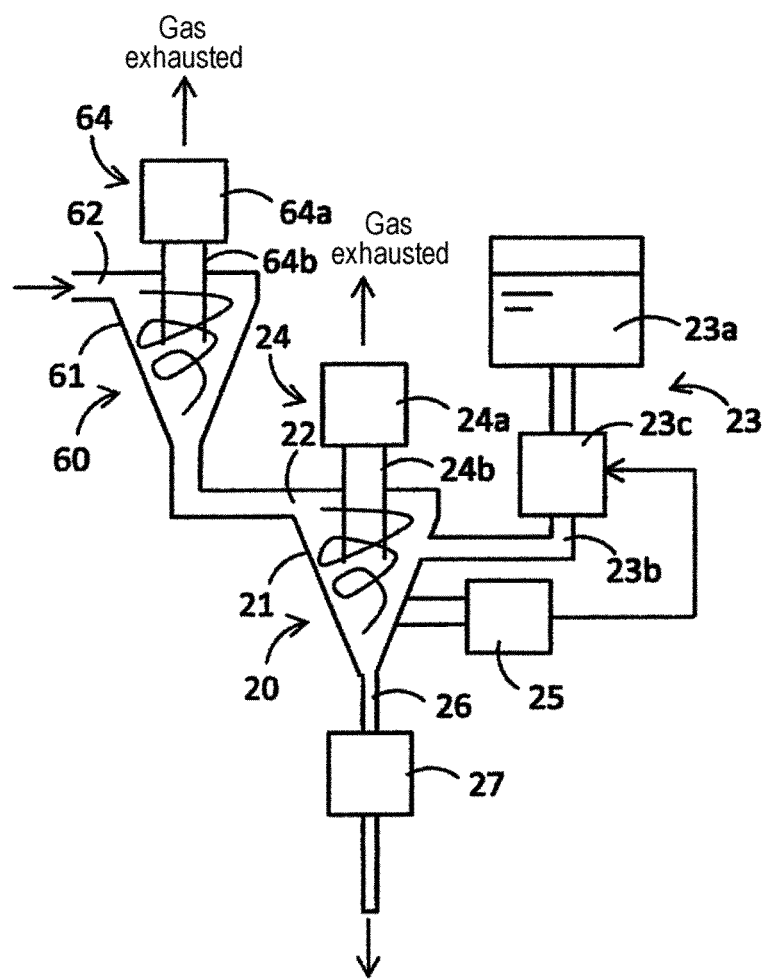

Furthermore, in the first embodiment, as illustrated in FIG. 1, the gas introduction part 22 of the cyclone 20 makes direct contact with the coarse-dust removal part 19 in the capturing part 12. However, the present disclosure is not limited thereto. As illustrated in FIG. 12, the capturing part 12 may include a second cyclone 60 equipped with a second cyclone body 61 and a second gas introduction part 62 for introducing a gas into the second cyclone body 61. The gas introduction part 22 of the cyclone 20 may be connected to the coarse-dust removal part 19 via the second cyclone 60 (a fourth embodiment).

In the illustrated example, the second cyclone body 61 includes a frusto-conical inner surface (hereinafter referred to as a "wall surface") and is oriented so that a small-diameter-side end portion is positioned below a large-diameter-side end portion.

The second gas introduction part 62 is installed in an upper portion of the second cyclone body 61 so as to extend in a tangential direction of the wall surface of the second cyclone body 61 and is gas-tightly connected to the coarse-dust removal part 19. The gas introduced from the coarse-dust removal part 19 into the second cyclone body 61 through the second gas introduction part 62 is guided along the wall surface of the second cyclone body 61 so that the gas swirls in the circumferential direction.

Above the second cyclone body 61, there is installed a second suction-exhaust part 64 configured to suction-exhaust and depressurize an interior of the second cyclone body 61 and configured to introduce the gas from the second gas introduction part 62 under a differential pressure so as to swirl in the circumferential direction.

The second suction-exhaust part 64 includes a second suction-exhaust pipe **64*b* coaxially inserted into the upper portion of the second cyclone body 61 and a second suction-exhaust pump 64*a* installed in the second suction-exhaust pipe 64*b***.

If the second suction-exhaust pump **64*a* is operated, the interior of the second cyclone body 61 is suction-exhausted and depressurized through the second suction-exhaust pipe 64*b*. Under the differential pressure between the interior and exterior of the second cyclone body 61, the gas existing outside the second cyclone body 61 is drawn from the second gas introduction part 62 into the second cyclone body 61 via the coarse-dust removal part 19. Then, the gas introduced into the second cyclone body 61 is guided along the wall surface of the second cyclone body 61 and is moved downward while swirling in the circumferential direction. That is to say, the gas forms a gas flow swirling in a spiral shape. At this time, the detection target particles existing in the gas are separated toward the wall surface of the second cyclone body 61 under a centrifugal force because the detection target particles have a relatively large specific gravity. The detection target particles impinge against the wall surface and fall down. On the other hand, the flow of a gas component having a relatively-small specific gravity is reversed in the lower portion of the second cyclone body 61 due to the frusto-conical shape of the wall surface of the second cyclone body 61, thereby forming an upward flow at the side of a center axis of the second cyclone body 61. Then, the gas component having a relatively-small specific gravity is discharged outside through the second suction-exhaust pipe 64*b***.

A lower portion of the second cyclone body 61 is gas-tightly connected to the gas introduction part 22 of the cyclone 20. The detection target particles falling down by impinging against the wall surface of the second cyclone body 61 are continuously supplied from the lower side of the second cyclone body 61 toward the gas introduction part 22 of the cyclone 20.

Specific examples according to the fourth embodiment will now be described.

In a third example of the fourth embodiment, while supplying a sampling gas containing particles of 180 nm in diameter that are generated by a particle generator to the second gas introduction part 62 of the second cyclone 60, the interior of the second cyclone body 61 was suction-exhausted at a flow rate of 600 SLM by the second suction-exhaust pump **64*b*, whereby a gas flow swirling in the circumferential direction was formed within the second cyclone body 61. Then, the concentration of the particles in the gas passing through the second gas introduction part 62 and the concentration of the particles in the gas supplied from the lower portion of the second cyclone body 61** toward the gas introduction part 22 of the cyclone 20 were respectively measured by a particle concentration measuring instrument.

Furthermore, in a fourth example of the fourth embodiment, the concentration of the particles in the gas passing through the second gas introduction part 62 and the concentration of the particles in the gas supplied from the lower portion of the second cyclone body 61 toward the gas introduction part 22 of the cyclone 20 were respectively measured by the same method as the third example except that the amount of the suction-exhaust performed by the second suction-exhaust pump 64b is changed to 900 SLM.

Moreover, in a fifth example of the fourth embodiment, the concentration of the particles in the gas passing through the second gas introduction part 62 and the concentration of the particles in the gas supplied from the lower portion of the second cyclone body 61 toward the gas introduction part 22 of the cyclone 20 were respectively measured by the same method as the third example except that the amount of the suction-exhaust performed by the second suction-exhaust pump 64b is changed to 1200 SLM.

The measurement results of the third example, the fourth example and the fifth example are collectively shown in Table 1 below.

TABLE 1

| | Third example | Fourth example | Fifth example |
| --- | --- | --- | --- |
| Suction-exhaust amount | 600 SLM | 900 SLM | 1200 SLM |
| Particle concentration in sampling gas (#/cc) | 1792 | 1195 | 896 |
| Enriched gas concentration (#/cc) | 7403 | 12253 | 19354 |
| Enrichment degree (times) | 4.1 | 10.3 | 21.6 |

As shown in Table 1, in any measurement result of the third example, the fourth example and the fifth example, the concentration of the particles in the gas supplied from the lower portion of the second cyclone body 61 toward the gas introduction part 22 of the cyclone 20 is larger than the concentration of the particles in the gas passing through the second gas introduction part 62. An effect that the particles are enriched by the second cyclone 60 was confirmed. Particularly, in the fifth example, it was confirmed that the concentration of the particles can be enriched 20 times.

As described above, according to the fourth embodiment, the gas containing the detection target particles enriched by the second cyclone 60 is supplied to the cyclone 20. Thus, the capturing efficiency of the detection target particles is further enhanced and the detection accuracy of the detection target particles is further improved.

Figure 14:
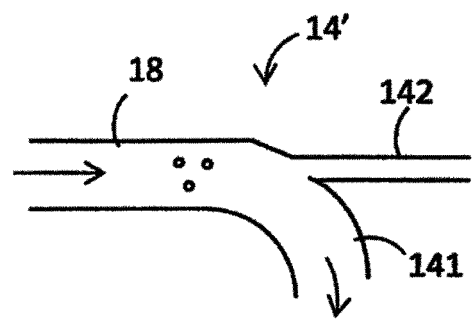

FIG. 14 is a schematic view illustrating the configuration of a droplet sorting part 14' of a measurement device according to a fifth embodiment of the present embodiment. Configurations of the measurement device according to the fifth embodiment other than the droplet sorting part 14' are substantially the same as the configurations of the measurement device according to the first embodiment. Thus, detailed descriptions thereof will be omitted.

As illustrated in FIG. 14, the droplet sorting part 14' is a chamber (inertia branch type spray chamber) configured to divide the gas flow into a gas flow containing large droplets and a gas flow containing small droplets using an inertial force. The droplet sorting part 14' includes a first flow path 141 connected to the downstream side of the main pipe 18 so as to be curved in a predetermined curvature with respect to the main pipe 18, and a second flow path 142 having a diameter smaller than the diameter of the first flow path 141 and connected to the downstream side of the main pipe 18 so as to extend parallel to the main pipe 18. The conductance of the first flow path 141 is larger than the conductance of the second flow path 142.

In the droplet sorting part 14' configured as above, the gas flow flowing through the main pipe 18 is guided along the first flow path 141 having a large conductance and is caused to swirl. At this time, the droplets having a diameter equal to or larger than a predetermined value, which are contained in the gas flow, are discharged outside through the second flow path 142 due to the inertial force thereof without following the swirling of the gas flow. Thus, the droplets having a diameter equal to or larger than a predetermined value are removed from the gas flow. The droplets having a diameter smaller than the predetermined value are carried by the gas flow and are supplied to the measurement part 15 while swirling the first flow path 141.

According to the fifth embodiment described above, the droplet sorting part 14' removes the droplets having a diameter equal to or larger than a predetermined value without causing the droplets to impinge against the inner surface of the chamber. It is therefore possible to suppress adhesion of the liquid to the inner surface of the chamber and contamination of the inner surface of the chamber. Thus, it is easy to perform maintenance of the measurement device.

Figure 15:
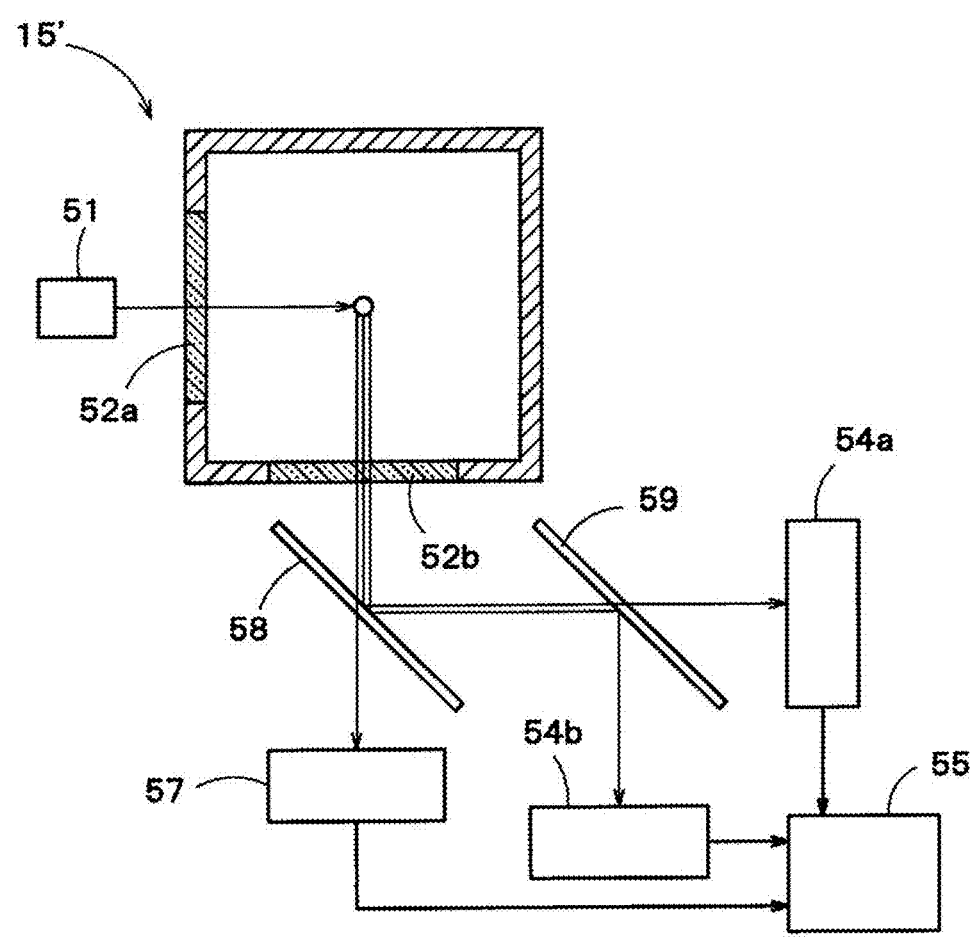

FIG. 15 is a schematic view illustrating the configuration of a measurement part 15' of a measurement device according to a sixth embodiment of the present disclosure. Configurations of the measurement device according to the sixth embodiment other than the measurement part 15' are substantially the same as the configurations of the measurement device according to the first embodiment. Thus, detailed descriptions thereof will be omitted.

As illustrated in FIG. 15, the measurement part 15' includes first and second optical filters 58 and 59, and first to third light-receiving parts 54a, 54b and 57 in place of the optical filter 53 and the light-receiving part 54 of the measurement part 15 illustrated in FIG. 4. Referring to FIG. 15, two light transmission windows 52a and 52b are disposed so as to make an angle of 90 degrees with each other (for example, the light transmission window 52a is disposed on a lateral side and the light transmission window 52b is disposed on a bottom side). Thus, the light emitted from the light-emitting part 51 and passed through the light transmission window 52a is not directly incident onto the light transmission window 52b.

The first optical filter 58 is installed outside the light transmission window 52b at a 45 degree-inclined orientation. The first optical filter 58 is configured to reflect the fluorescent light emitted from the fluorescent substance and to transmit the light (namely, the scattered light coming from the droplets) having a wavelength differing from the wavelength of the fluorescent light emitted from the fluorescent substance. The third light-receiving part 57 is disposed at the opposite side of the first optical filter 58 from the light transmission window 52b. The third light-receiving part 57 is configured to receive the light transmitted through the first optical filter 58 and to convert the light to an electrical signal.

Furthermore, the second optical filter 59 is installed at the right side of the first optical filter 58 in FIG. 15 at a 45 degree-inclined orientation. The second optical filter 59 is configured to transmit the light of a first wavelength range reflected by the first optical filter 58 and to reflect the light of a second wavelength range differing from the first wavelength range. The first light-receiving part 54*a* is disposed at the right side of the second optical filter 59 in FIG. 15. The first light-receiving part 54*a* is configured to receive the light transmitted through the second optical filter 59 and to convert the light to an electrical signal. Furthermore, the second light-receiving part 54*b* is disposed at the lower side of the second optical filter 59 in FIG. 15. The second light-receiving part 54*b* is configured to receive the light reflected by the second optical filter 59 and to convert the light to an electrical signal.

The first to third light-receiving parts 54*a*, 54*b* and 57 are, for example, photomultiplier tubes and are configured to output, for example, an electric current of a signal level corresponding to the light reception intensity, to the light reception output measuring part 55.

According to the sixth embodiment described above, a first fluorescent substance which emits fluorescent light of a first wavelength range and a second fluorescent substance which emits fluorescent light of a second wavelength range are bonded to detection target particles of the same kind (e.g., noroviruses). In this state, the fluorescence intensity of the droplets is detected in the first wavelength range and the second wavelength range. This makes it possible to accurately detect the detection target particles.

Furthermore, a first fluorescent substance which emits fluorescent light of a first wavelength range is bonded to first detection target particles (e.g., noroviruses) and a second fluorescent substance which emits fluorescent light of a second wavelength range is bonded to second detection target particles (e.g., influenza viruses). In this state, the fluorescence intensity of the droplets is detected in the first wavelength range and the second wavelength range. This makes it possible to simultaneously detect two kinds of detection target particles.

Furthermore, by detecting the intensity of the light (namely, the scattered light coming from the droplets) having a wavelength differing from the wavelength of the fluorescent light emitted from the fluorescent substance, it is possible to make a debris determination. Additional descriptions will be made on the debris determination. There may be a case where the wavelength of auto fluorescent light emitted from so-called debris such as clothing scraps or the like overlaps with the wavelength of the fluorescent light emitted from the fluorescent substance. In this case, there is sometimes the case that the auto fluorescent light of the debris is detected by the first light-receiving part 54*a* and/or the second light-receiving part 54*b*. However, the debris is relatively large and the scattered light is also large. Thus, the large scattered light may well be detected by the third light-receiving part 57. Accordingly, when the fluorescent light is detected by the first light-receiving part 54*a* and/or the second light-receiving part 54*b* and the large scattered light is detected by the third light-receiving part 57, it is determined that the debris exists. This makes it possible to reduce noise attributable to the auto fluorescent light of the debris and to further improve the detection accuracy of the detection target particles.

While in the present embodiment, the fluorescence intensity has been described to be measured in two different wavelength ranges (the first wavelength range and the second wavelength range), the fluorescence intensity may be measured in three or more different wavelength ranges.

Figure 16:
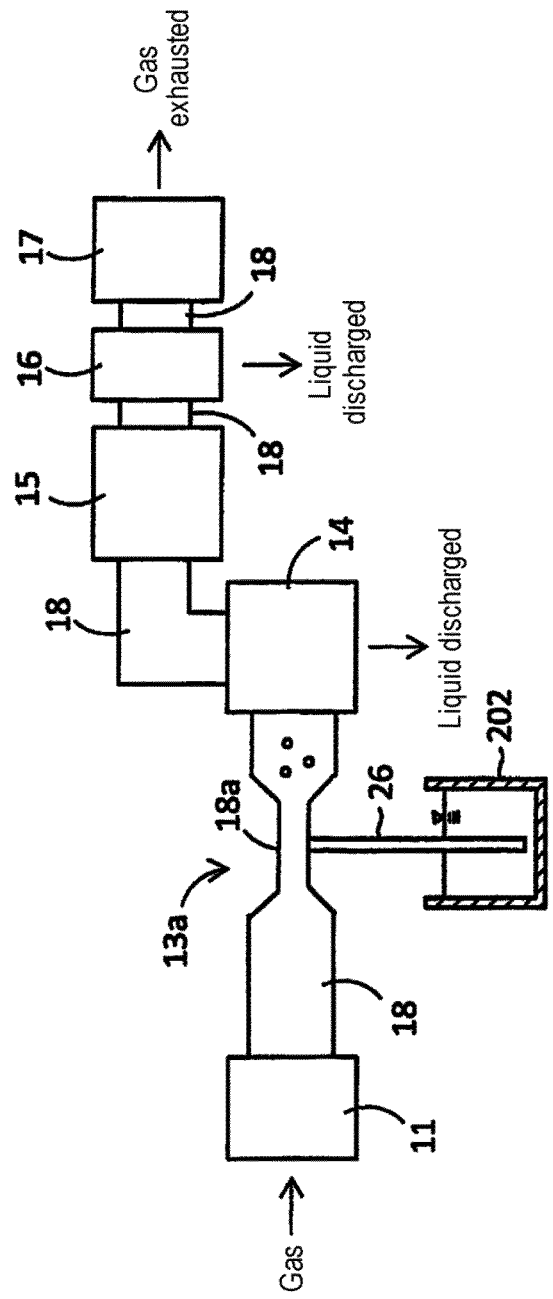
Figure 17:
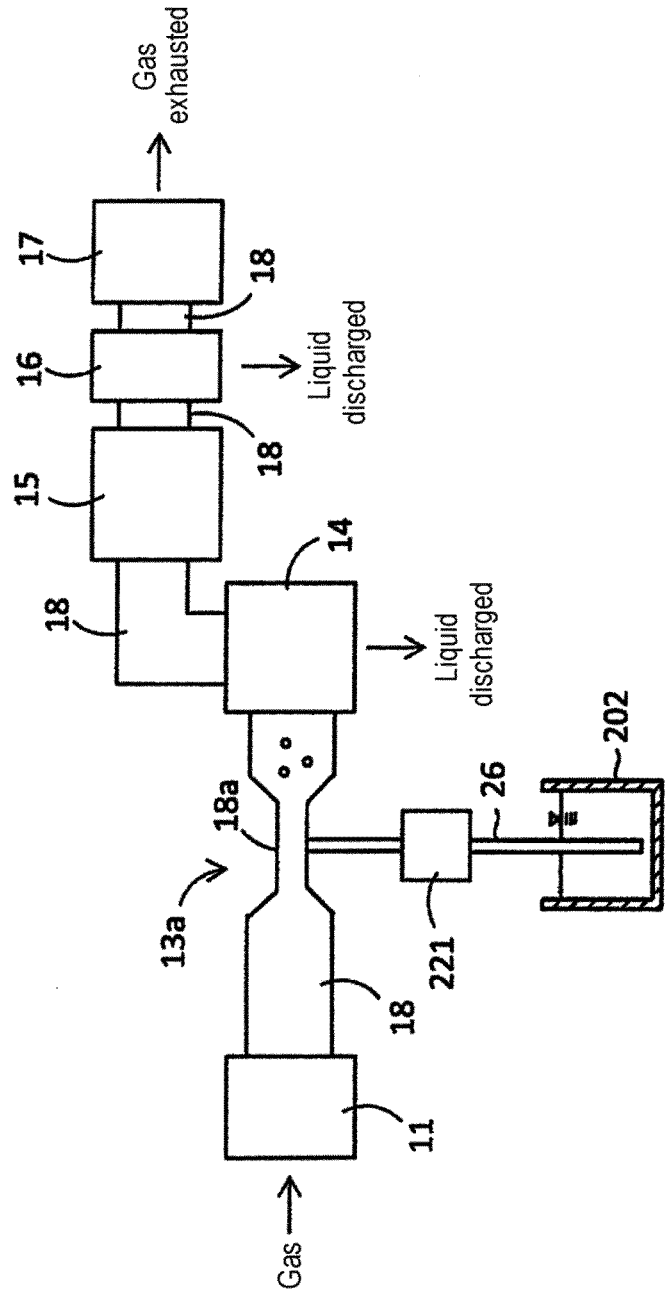
Figure 18:
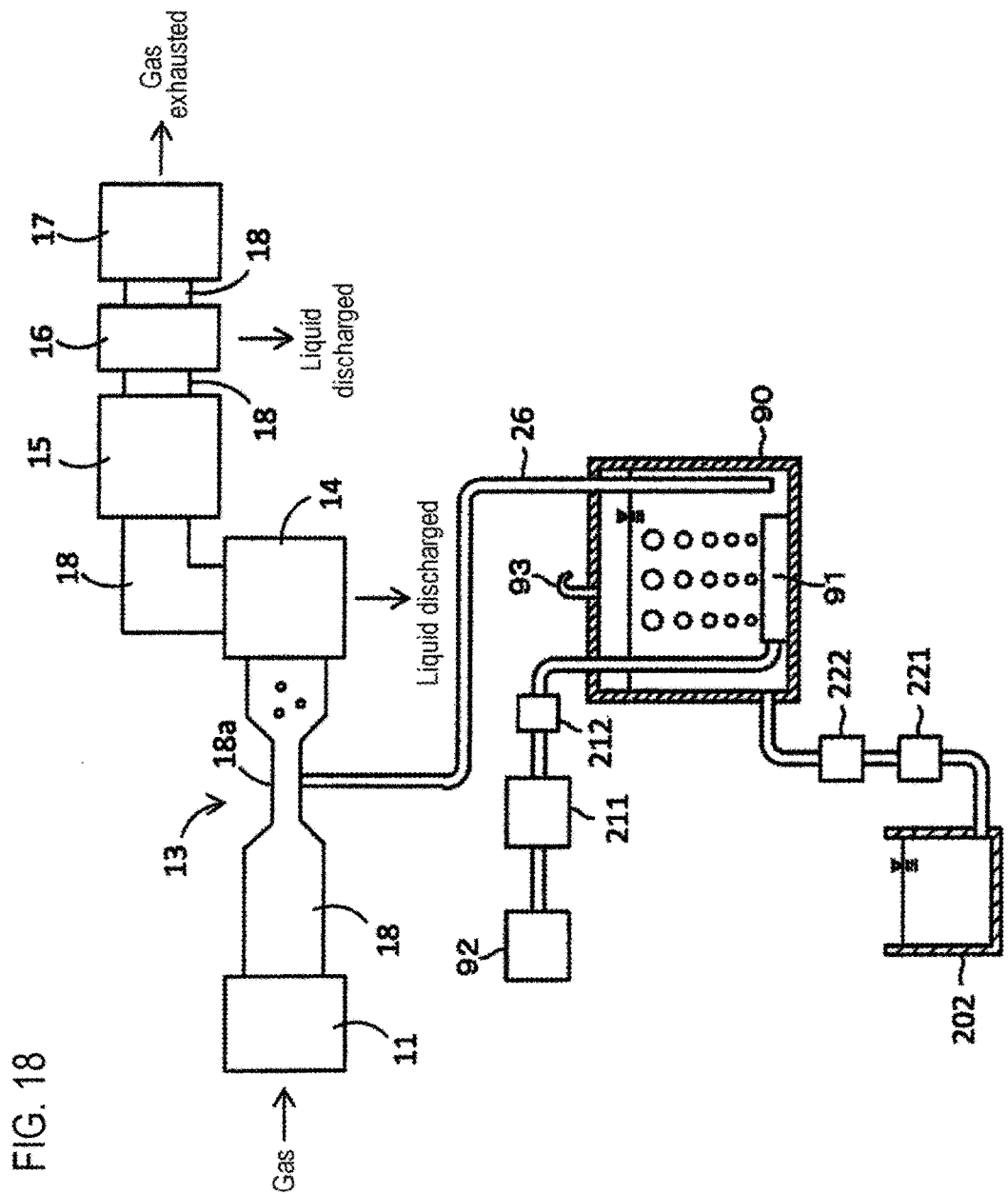

FIG. 16 is a schematic view illustrating the configuration of a measurement device according to a seventh embodiment of the present disclosure.

In the measurement device illustrated in FIG. 16, one end of the liquid supply pipe 26 is immersed in a liquid storage tank 202 which accommodates a liquid containing a fluorescent substance specifically bondable to detection target particles and the other end of the liquid supply pipe 26 is connected to the throttle portion 18*a* of the main pipe 18 similar to the first embodiment, thereby forming a droplet forming part 13*a*.

In this case, the end of the liquid supply pipe 26 connected to the throttle portion 18*a* is kept at a negative pressure by the gas flow formed within the main pipe 18 by the suction pump 17. Thus, the liquid accommodated in the liquid storage tank 202 is drawn into the main pipe 18 through the liquid supply pipe 26, whereby aerosol-like liquid droplets are formed. The detection target particles existing in the gas flow, when passing through the throttle portion 18*a* of the main pipe 18, are brought into the liquid split from the end of the liquid supply pipe 26 connected to the throttle portion 18*a*. Accordingly, the capturing of the detection target particles in the liquid is performed by the droplet forming part 13*a*. Thus, in this example, it can be said that the droplet forming part 13*a* serves as a capturing part. The aerosol-like liquid droplets formed by the droplet forming part 13*a* are carried by the gas flow flowing through the main pipe 18 and are sent to the droplet sorting part 14 where droplets having a diameter smaller than a predetermined value are sorted. Even in this example, it is possible to achieve effects similar to those of the aforementioned embodiments.

Furthermore, for example, as illustrated in FIG. 17, in the example in which the droplet forming part 13*a* serves as a capturing part, a liquid feeding pump 221 may be installed in the liquid supply pipe 26 and the liquid accommodated in the liquid storage tank 202 may be fed to the droplet forming part 13*a* with the liquid feeding operation of the liquid feeding pump 221.

Furthermore, for example, as illustrated in FIG. 18, an aeration tank 90 may be used as the capturing part 12. FIG. 18 is a view illustrating one example of a measurement device in which the aeration tank 90 is used as the capturing part 12.

In the illustrated example, the liquid accommodated in the liquid storage tank 202 is supplied into the aeration tank 90 via the liquid feeding pump 221 and a liquid flow rate control part 222. Furthermore, an inspection target gas is sucked from a gas inlet port 92 by a suction operation of a suction pump 211 and is sent to a gas diffuser 91 via a gas flow rate control part 212. Then, in the liquid accommodated in the aeration tank 90, the inspection target gas and the liquid are brought into contact with each other by the gas diffuser 91. Thus, the detection target particles existing in the gas are captured by the liquid. In FIG. 18, reference numeral 93 designates a ventilation port. In this case, as illustrated, one end of the liquid supply pipe 26 may be immersed into the aeration tank 90 and the liquid may be drawn from the end of the liquid supply pipe 26, connected to the throttle portion 18*a*, into the main pipe 18 using the gas flow generated by the suction operation of the suction pump 17, thereby forming droplets. In some embodiments, as illustrated in FIG. 17, a liquid feeding pump may be installed in the liquid supply pipe 26.

In the embodiments described above, there is described, by way of example, a case where the detection target particles are detected from the inspection target gas. However, the present disclosure is not limited thereto. The substance to be inspected (the specimen) may be a liquid. Describing one more specific example, the substance to be inspected may be a liquid, or a solution mixed in advance with the substance to be inspected may be used as an inspection target.

Figure 19:
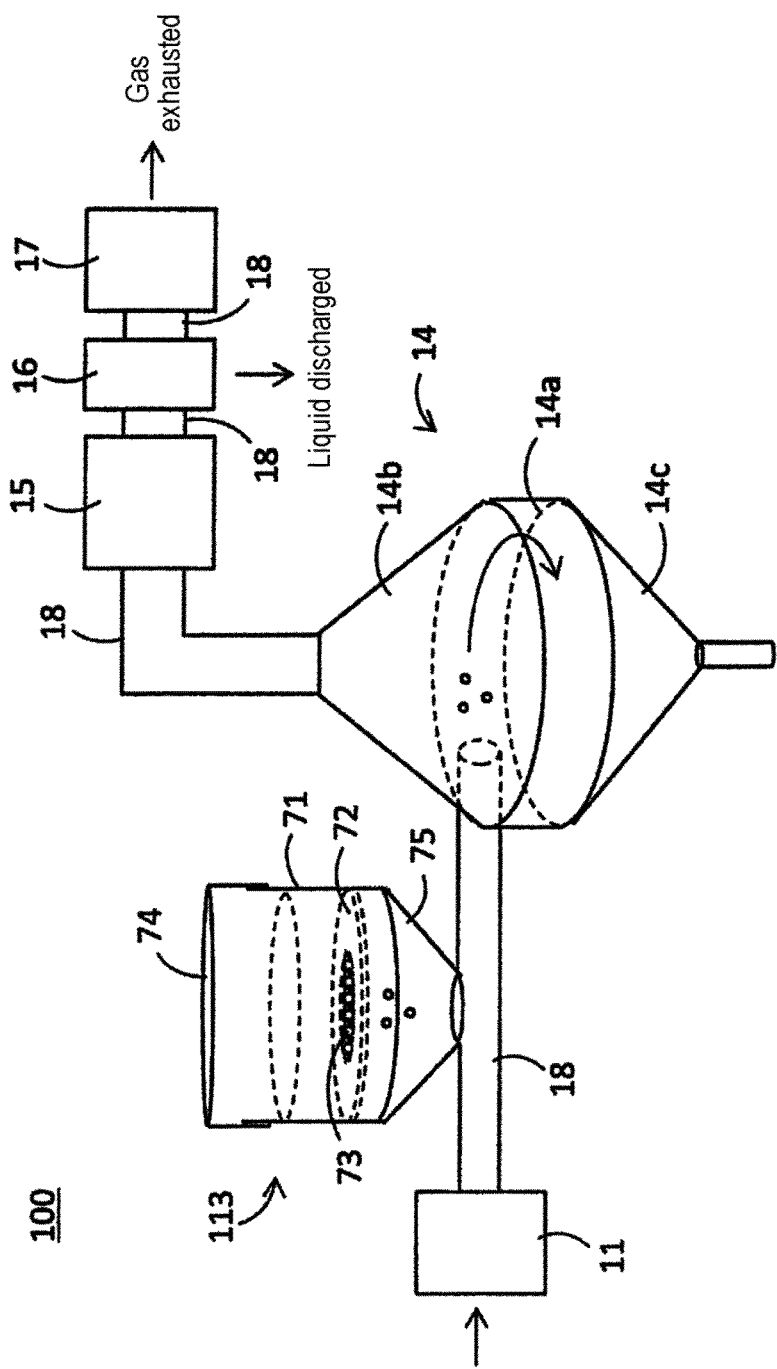
Figure 20:
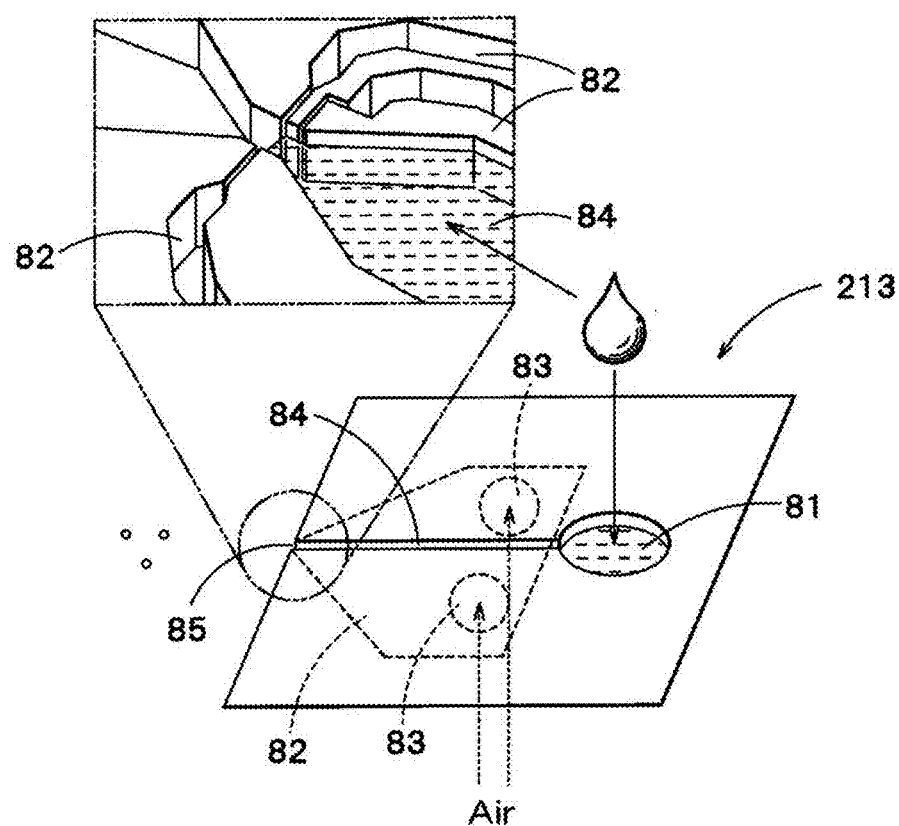

For example, as illustrated in FIG. 19, a measurement device 100 may include, instead of the capturing part 12 and the droplet forming part 13 of the measurement device 10 illustrated in FIG. 1, a droplet forming part 113 configured to form aerosol-like liquid droplets from a liquid in which a specimen and a fluorescent substance specifically bondable to detection target particles are mixed with each other (an eighth embodiment).

The droplet forming part 113 includes a small cylindrical liquid accommodation part 71 having a capacity of 0.1 ml to 5 ml, a ring-shape piezoelectric vibrator 72 fitted to a lower end portion of the liquid accommodation part 71, and a mesh-like plate 73 fixed to an inner side of a ring of the piezoelectric vibrator 72. A lid 74 is installed in an upper end portion of the liquid accommodation part 71 so that extraneous materials do not enter the liquid accommodation part 71. A power source (not shown) is electrically connected to the piezoelectric vibrator 72.

When a voltage is not applied from the power source (not shown) to the piezoelectric vibrator 72, the liquid accommodated in the liquid accommodation part 71 does not flow outward from small holes of the mesh-like plate 73 due to the surface tension thereof.

On the other hand, when a voltage is applied from the power source (not shown) to the piezoelectric vibrator 72, the piezoelectric vibrator 72 and the mesh-like plate 73 vibrate in a frequency range of ultrasonic waves. The liquid accommodated in the liquid accommodation part 71 falls down as aerosol-like liquid droplets from the small holes of the mesh-like plate 73 as the vibration of the mesh-like plate 73 is propagated to the liquid.

An upper end portion of a truncated conical guide member 75 is connected to a lower end portion of the liquid accommodation part 71. A lower end portion of the guide member 75 is connected to the main pipe 18.

In FIG. 19, the same parts as those of the first embodiment illustrated in FIG. 1 are designated by like reference numerals with the detailed descriptions thereof omitted.

Next, descriptions will be made on the operation of the measurement device 100 configured as above.

First, as illustrated in FIG. 19, the lid 74 of the droplet forming part 113 is removed from the upper end portion of the liquid accommodation part 71. The liquid in which a liquid-phase or solid-phase specimen and a fluorescent substance specifically bondable to detection target particles are mixed with each other, is accommodated in the liquid accommodation part 71 at a volume of 0.1 ml to 5 ml. For example, blood, saliva, cerebrospinal fluid, urine, cells or the like is used as the liquid-phase or solid-phase specimen. Thereafter, the lid 74 is placed on the upper end portion of the liquid accommodation part 71.

Subsequently, a gas (e.g., an air) is drawn into the main pipe 18 via the dust removal part 11 by the suction pump 17, thereby forming a gas flow which flows through the droplet forming part 113, the droplet sorting part 14, the measurement part 15 and the liquid recovery part 16 in the named order. The gas flow is exhausted via the suction pump 17 and a filter (not shown).

Then, the piezoelectric vibrator 72 of the droplet forming part 113 and the mesh-like plate 73 vibrate in a frequency range of ultrasonic waves. The liquid accommodated in the liquid accommodation part 71 falls down as aerosol-like liquid droplets from the small holes of the mesh-like plate 73.

The aerosol-like liquid droplets formed by the droplet forming part 113 are guided by the guide member 75 and are supplied to the main pipe 18. The aerosol-like liquid droplets are carried by the gas flow flowing through the main pipe 18 and are sent to the droplet sorting part 14.

In the droplet sorting part 14, the gas flow containing the droplets supplied from the droplet forming part 113 are guided along the cylindrical inner surface of the central chamber body **14*a* and are caused to swirl in the circumferential direction. At this time, the droplets having a diameter equal to or larger than a predetermined value, which are contained in the gas flow, are separated toward the inner surface of the central chamber body 14*a* under a centrifugal force. The droplets impinge against and adhere to the inner surface. On the other hand, the droplets having a diameter smaller than the predetermined value are moved upward together with the gas flow while swirling in the circumferential direction and are supplied to the measurement part 15 from the upper side of the upper chamber body 14*b***.

Thereafter, according to the same process as the process of the first embodiment, the fluorescence intensity of the droplets is measured in the measurement part 15. Based on the measurement result, it is determined whether the detection target particles are contained in the specimen. The droplets passed through the measurement part 15 are separated into a gas and a liquid by the liquid recovery part 16. The liquid is recovered. On the other hand, the gas is exhausted outside the measurement device 10 by the suction pump 17 installed at the downstream side of the liquid recovery part 16.

According to the eighth embodiment described above, ultrasonic vibration is used in the droplet forming part 113. It is therefore possible to efficiently form aerosol-like liquid droplets from a small amount, e.g., 0.1 ml to 5 ml, of liquid.

Furthermore, in the present embodiment, the gas flow flowing through the main pipe 18 is formed by the suction pump 17 installed at the downstream-side end portion of the main pipe 18. However, the present disclosure is not limited thereto. For example, a compressed gas introduction part may be connected to the upstream-side end portion of the main pipe 18. By introducing a compressed gas of about 3 atm from the compressed gas introduction part, a gas flow flowing through the main pipe 18 may be formed.

FIG. 20 is a schematic view illustrating a modification of the droplet forming part 113. In FIG. 20, the droplet forming part is designated by reference numeral 213.

The droplet forming part 213 illustrated in FIG. 20 is formed of a MEMS. The droplet forming part 213 includes a small recess-shaped liquid accommodation part 81 having a capacity of 0.1 ml to 5 ml, a liquid flow path 84 having a width of 1 mm or less and communicating with the liquid accommodation part 81, a gas flow path 82 installed in the tip portion of the liquid flow path 84 so as to merge with the liquid flow path 84, and a compressed gas introduction port 83 configured to introduce a compressed gas into the gas flow path 82. The term "MEMS" used herein refers to a micro-electro-mechanical system formed on one chip using a semiconductor processing technique. The MEMS is in compliance with the content stipulated in JIS C5630-1.

The liquid in which a liquid-phase or solid-phase specimen and a fluorescent substance specifically bondable to detection target particles are mixed with each other, is accommodated in the liquid accommodation part 81 at a volume of 0.1 ml to 5 ml. For example, blood, saliva, cerebrospinal fluid, urine, cells or the like is used as the liquid-phase or solid-phase specimen. The liquid accommodated in the liquid accommodation part 81 is moved to the tip of the liquid flow path 84 by a capillary action.

A compressed gas of about 7 atm is introduced from the compressed gas introduction port 83. The compressed gas thus introduced passes through the gas flow path 82 and is discharged from the tip portion of the liquid flow path 84 to the outside. At this time, a negative pressure is generated in the tip portion of the liquid flow path 84 by a venturi effect. The liquid existing within the liquid flow path 84 is sucked and split by the negative pressure. Thus, aerosol-like liquid droplets are formed from the liquid accommodated in the liquid accommodation part 81.

According to this embodiment, it is therefore possible to efficiently form aerosol-like liquid droplets from a small amount, e.g., 0.1 ml to 5 ml, of liquid.

Furthermore, for example, in the seventh embodiment, there has been described, by way of example, a case where the droplet forming part 113 forms droplets using ultrasonic waves. However, as mentioned above, the present disclosure is not limited thereto. The droplet forming part 113 may form droplets using an arbitrary technique as long as it can form a droplet group including droplets having a diameter less than 20 μm. Moreover, depending on the measurement target or the measurement purpose, it may be possible to form droplets having a diameter less than 50 μm. For example, the droplet forming part may form a group of aerosol-like liquid droplets using at least one of a nebulizer, an electrospray, a two-fluid nozzle, a piezoelectric element (e.g., a bubble jet (registered trademark)), ultrasonic waves and a depressurization process. The minimum diameter of the droplets that can be formed by the aforementioned droplet forming means is about 3 nm. In particular, if the droplets are formed using the electrospray, it is possible to form the droplets having a diameter of 3 nm or more and 50 μm or less with enhanced controllability.

Figure 21:
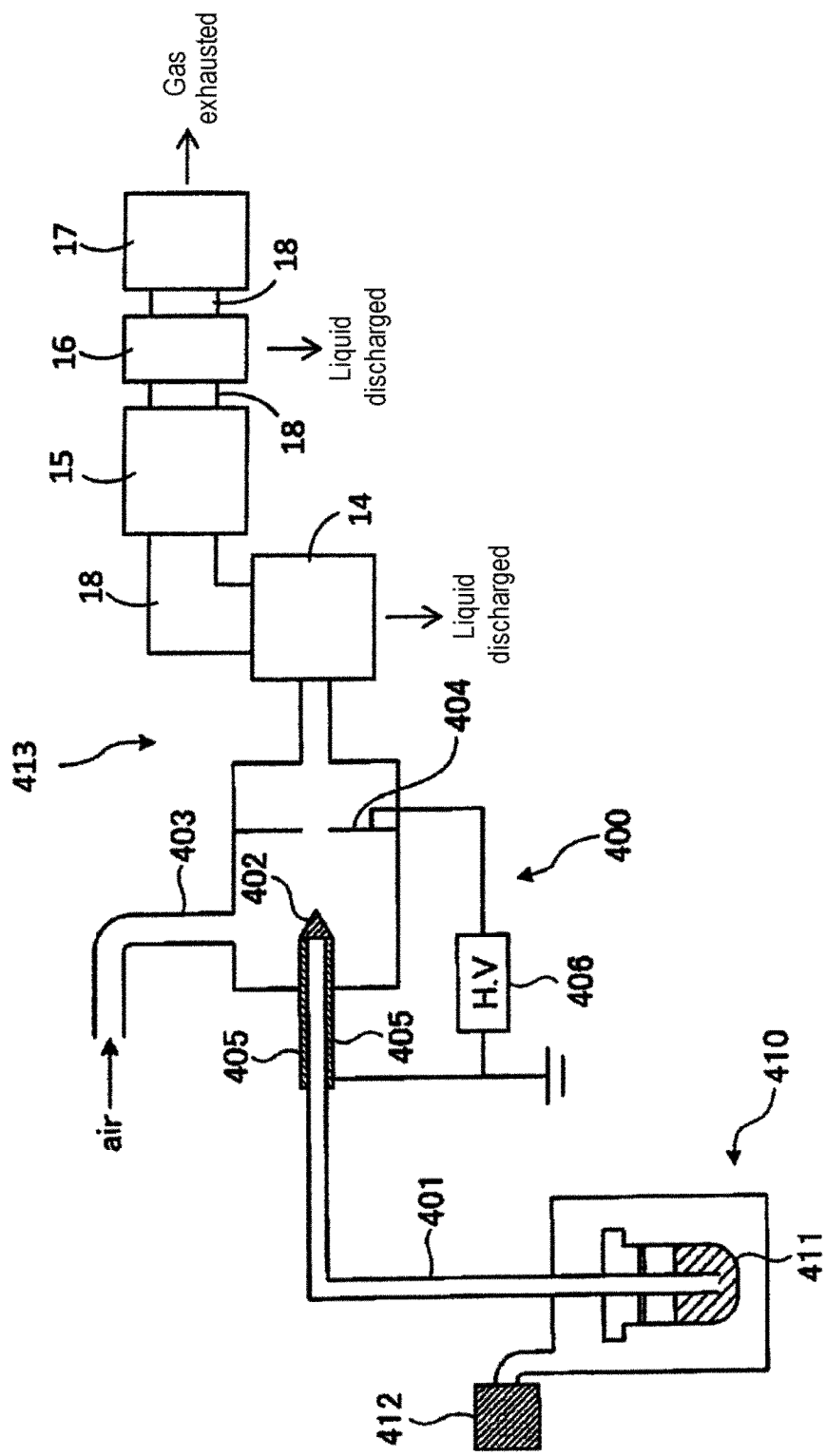
Figure 22:
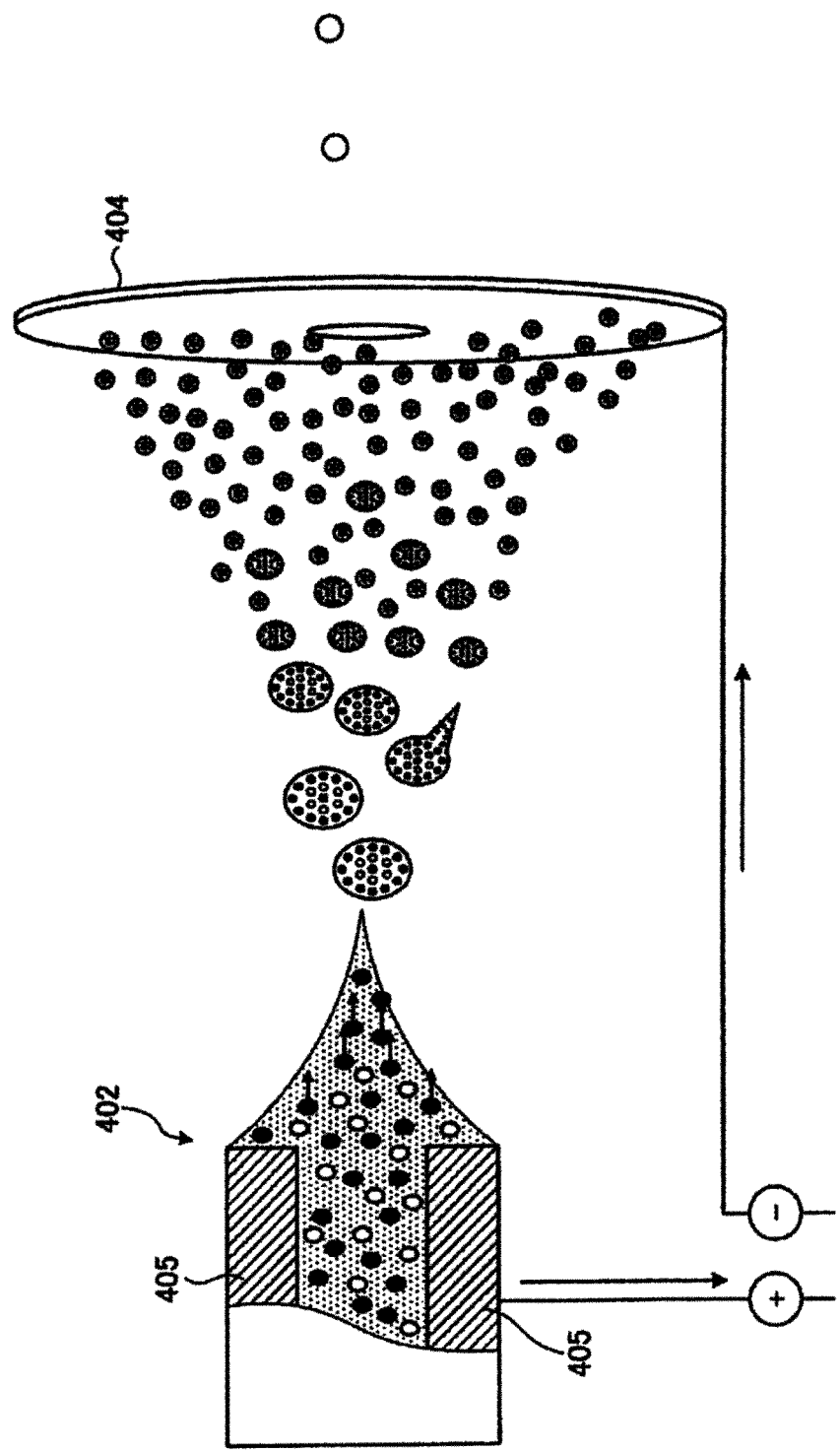

FIGS. 21 and 22 are views illustrating one example of the configuration of the measurement device in the case where droplets are formed using an electrospray. In the example illustrated in FIG. 21, the measurement device includes an electrospray 400 as a droplet forming part 413, and a sample providing part 410 configured to provide a liquid to the electrospray 400.

In the example illustrated in FIG. 21, the sample providing part 410 includes a vial 411 configured to hold a liquid in which a specimen and a fluorescent substance specifically bondable to detection target particles are mixed with each other, and a pressure part 412 configured to apply pressure to the vial 411. Furthermore, in the example illustrated in FIG. 21, one end of a capillary 401 configured to supply the liquid held by the vial 411 to a discharge part 402 is put into the liquid held by the vial 411.

Furthermore, in the example illustrated in FIG. 21, the electrospray 400 includes the capillary 401, the liquid discharge part 402 installed at the other end of the capillary 401, a gas inlet port 403, an electrode 404 installed in the capillary 401, an electrode 405 installed in a discharge direction in which the liquid is discharged from the discharge part 402, and a voltage supply part 406.

As illustrated in FIG. 22, the voltage supply part 406 is configured to supply voltages to the electrode 404 and the electrode 405. For example, the voltage supply part 406 supplies a positive voltage to the electrode 404 and supplies a negative voltage to the electrode 405. As a result, a strong electric field is generated in the discharge part 402 which is a tip portion of the capillary 401.

When the droplet forming part 413 forms droplets, the pressure part 412 applies a pressure to the vial 411 so that the liquid is supplied from the vial 411 to the electrospray 400 through the capillary 401. Since a strong electric field is generated in the discharge part 402, ions having electric charges are gathered on the surface of the liquid, thereby forming a cone. This cone is called a Taylor cone. Thereafter, droplets are formed and discharged from the discharge part 402.

In the example illustrated in FIG. 22, the electrode 405 has a hole formed in the central portion thereof. Thus, the droplets passed through the hole of the central portion of the electrode 405 among the droplets discharged from the discharge part 402 are sent to the droplet sorting part 14 and are then sent to the measurement part 15. In addition, the diameter of the droplets discharged from the discharge part 402 grows small as a volatile solvent is subsequently evaporated.

The configuration of the measurement device including the electrospray 400 is not limited to the example illustrated in FIGS. 21 and 22 but may be an arbitrary configuration. For example, in the example illustrated in FIGS. 21 and 22, there is illustrated, by way of example, a case where the liquid held in the vial 411 is supplied to the electrospray 400 as the pressure part 412 applies pressure. However, the present disclosure is not limited thereto. For example, the liquid may be supplied to the electrospray 400 by installing a separate pump or may be supplied using an arbitrary technique. Furthermore, in the example illustrated in FIGS. 21 and 22, there is illustrated, by way of example, a case where the gas is introduced from the gas inlet port 403. However, the present disclosure is not limited thereto. For example, a clean gas may be provided, or a clean gas and $CO_2$ may be supplied into the electrospray 400. Furthermore, in the example illustrated in FIGS. 21 and 22, there is illustrated, by way of example, a case where the electrode 405 is installed in the discharge direction in which the liquid is discharged from the discharge part 402. However, the present disclosure is not limited thereto. For example, the electrode 405 may be installed along the discharge direction in which the liquid is discharged from the discharge part 402. For example, in the example illustrated in FIG. 21, the inner wall of the electrospray 400 may be used as the electrode 405.

EXPLANATION OF REFERENCE NUMERALS

10: measurement device, 100: measurement device, 11: dust removal part, 12: capturing part, 13: droplet forming part, 13a: droplet forming part, 113: droplet forming part, 213: droplet forming part, 413: droplet forming part, 14: droplet sorting part, 14': droplet sorting part, 14a: central chamber body, 14b: upper chamber body, 14c: lower chamber body, 141: first flow path, 142: second flow path, 15: measurement part, 15': measurement part, 16: liquid recovery part, 17: suction pump, 18: main pipe, 18a: throttle portion, 19: coarse-dust removal part, 20: cyclone, 21: cyclone body, 22: gas introduction part, 23: liquid introduction part, 23a: tank, 23b: liquid introduction pipe, 23c: flow rate control part, 24: suction exhaust part, 24a: suction exhaust pump, 24b: suction exhaust pipe, 25: level detection part, 26: liquid supply pipe, 27: liquid feeding pump, 41: second liquid introduction part, 42: impeller (propeller), 43: rotational drive part, 44: swirling part, 45: exhaust hole, 46: heating mechanism, 51: light-emitting part, 52a: light transmission window, 52b: light transmission window, 53: optical filter, 54: light-receiving part, 54a: first light-receiving part, 54b: second light-receiving part, 55: light reception output measuring part, 56: case body, 57: third light-receiving part, 58: first optical filter, 59: second optical filter, 60: second cyclone, 61: second cyclone body, 62: second gas introduction part, 64: second suction exhaust part, 64a: second suction exhaust pump, 64b: second suction exhaust pipe, 71: liquid accommodation part, 72: piezoelectric vibrator, 73: mesh-like plate, 74: lid, 75: guide member, 81: liquid accommodation part, 82: gas flow path, 83: compressed gas introduction port, 84: liquid flow path, 90: aeration tank, 91: gas diffuser, 92: gas inlet port, 93: ventilation port, 202: liquid storage tank, 211: suction pump, 212: gas flow rate control part, 221: liquid feeding pump, 222: liquid flow rate control part, 301: droplet, 302: droplet, 303: portion containing fluorescent substance not bonded to detection target particles, 304: portion containing fluorescent substance bonded to detection target particles, 311: droplet, 312: droplet, 313: portion containing fluorescent substance bonded to detection target particles, 314: portion containing fluorescent substance not bonded to detection target particles, 400: electrospray, 401: capillary, 402: discharge part, 403: gas inlet port, 404: electrode, 405: electrode, 406: voltage supply part, 410: sample providing part, 411: vial, 412: pressure part

What is claimed is:

1. A measurement device, comprising:
   a droplet forming part configured to form aerosol-like liquid droplets from a liquid in which a fluorescent substance specifically bondable to detection target particles and a specimen are mixed with each other;
   a droplet sorting part configured to sort and select droplets having a diameter smaller than a predetermined value from the droplets formed by the droplet forming part; and
   a measurement part configured to irradiate light onto the droplets selected by the droplet sorting part and configured to measure the fluorescence intensity of the droplets, the measurement part including a case body through which the droplets selected by the droplet sorting part flow, a light-emitting part irradiating the light to the cased body, and a light-receiving part receiving fluorescent light from the fluorescent substance when the light is irradiated to the case body,
   wherein the droplet sorting part includes a spray chamber configured to sort and select the droplets having the diameter smaller than the predetermined value using an inertial force, and supply only the droplets having the diameter smaller than the predetermined value to the measurement part,
   wherein the droplet sorting part is configured to sort and select droplets having a diameter of less than 20 µm, and
   wherein the spray chamber includes a central chamber body having a cylindrical inner surface, a main pipe communicating between the droplet forming part and the droplet sorting part, the main pipe being connected to the cylindrical inner surface in such an orientation as to extend in a tangential direction of the cylindrical inner surface so that the droplets introduced into the central chamber body through the main pipe are guided along the cylindrical inner surface under the inertial force and are caused to swirl in a circumferential direction while droplets having a diameter equal to or larger than the predetermined value impinge the cylindrical inner surface and are removed, and only the droplets having the diameter smaller than the predetermined value are supplied toward the measurement part.

2. The device of claim 1, further comprising:
   a capturing part configured to cause the liquid to capture the detection target particles contained in a gas, cause the fluorescent substance specifically bondable to the detection target particles to be bonded to the detection target particles existing in the liquid, and supply the liquid in which the fluorescent substance and the detection target particles are mixed with each other, to the droplet forming part, the capturing part including a cyclone having a cyclone body, a gas introduction part for introducing the gas into the cyclone body and a liquid introduction part for introducing the liquid into the cyclone body.

3. The device of claim 1, wherein the droplet forming part includes a liquid accommodation part in a cylindrical shape having a capacity of 0.1 ml to 5 ml and configured to accommodate the liquid in which the fluorescent substance specifically bondable to the detection target particles and the specimen are mixed with each other, a ring-shaped piezoelectric vibrator fitted to a lower end portion of the liquid accommodation part, and a mesh-like plate fixed to an inner side of a ring of the piezoelectric vibrator.

4. The device of claim 1, wherein the droplet forming part includes a liquid accommodation part in a recess like shape having a capacity of 0.1 ml to 5 ml and configured to accommodate the liquid in which the fluorescent substance specifically bondable to the detection target particles and the specimen are mixed with each other, a liquid flow path having a width of 1 mm or less and communicating with the liquid accommodation part, a gas flow path installed so as to merge with the liquid flow path in a tip portion of the liquid flow path, and a compressed gas introduction port configured to introduce a compressed gas into the gas flow path.

5. The device of claim 1, wherein the measurement part is configured to measure the fluorescence intensity of the droplets in two or more kinds of different wavelength ranges.

6. The device of claim 1, wherein the measurement part is configured to measure the fluorescence intensity of the droplets and an intensity of a scattered light coming from the droplets.

7. The device of claim 1, wherein the fluorescent substance is a fluorescence-labeled antibody.

8. The device of claim 1, wherein the fluorescent substance is an antibody agglomeration particle whose surface is modified with a plurality of fluorescence-labeled antibodies.

9. The device of claim 1, wherein the droplet forming part forms the aerosol-like liquid droplets using at least one of a nebulizer, an electrospray, a two-fluid nozzle, a piezoelectric element, an ultrasonic wave and a depressurization treatment.

10. A measurement method, comprising:
    a droplet forming step of forming aerosol-like liquid droplets from a liquid in which a fluorescent substance specifically bondable to detection target particles and a specimen are mixed with each other;
    a droplet sorting step of sorting and selecting droplets having a diameter smaller than a predetermined value from the droplets formed at the droplet forming step; and
    a measurement step of irradiating light onto the droplets selected through the droplet sorting step and measuring the fluorescence intensity of the droplets,
    wherein, in a spray chamber, the droplet sorting step sorts and selects the droplets having the diameter smaller than the predetermined value using an inertial force, and supplies only the droplets having the diameter smaller than the predetermined value to the measurement step, wherein the droplet sorting step sorts and selects droplets having a diameter less than 20 μm, and wherein the spray chamber includes a central chamber body having a cylindrical inner surface, a main pipe communicating between the droplet forming part and the droplet sorting part, the main pipe being connected to the cylindrical inner surface in such an orientation as to extend in a tangential direction of the cylindrical inner surface so that the droplets introduced into the central chamber body through the main pipe are guided along the cylindrical inner surface under the inertial force and are caused to swirl in a circumferential direction while droplets having a diameter equal to or larger than the predetermined value impinge the cylindrical inner surface and are removed, and only the droplets having the diameter smaller than the predetermined value are supplied toward the measurement part.

11. The method of claim 10, wherein the fluorescent substance is a fluorescence-labeled antibody.

12. The method of claim 10, wherein the fluorescent substance is an antibody agglomeration particle whose surface is modified with a plurality of fluorescence-labeled antibodies.

* * * * *